United States Patent
Frankard et al.

(10) Patent No.: US 7,932,432 B2
(45) Date of Patent: Apr. 26, 2011

(54) SEEDY 1 NUCLEIC ACIDS FOR MAKING PLANTS HAVING CHANGED GROWTH CHARACTERISTICS

(75) Inventors: Valerie Frankard, Sint-Genesius-Rode (BE); Vladimir Mironov, Ghent (BE)

(73) Assignee: Crop Design N.V., Zwijnaarde (BE)

( * ) Notice: Subject to any disclaimer, the term of this patent is extended or adjusted under 35 U.S.C. 154(b) by 987 days.

(21) Appl. No.: 10/580,085

(22) PCT Filed: Nov. 19, 2004

(86) PCT No.: PCT/EP2004/053030
§ 371 (c)(1),
(2), (4) Date: May 9, 2007

(87) PCT Pub. No.: WO2005/049646
PCT Pub. Date: Jun. 2, 2005

(65) Prior Publication Data
US 2009/0235393 A1    Sep. 17, 2009

Related U.S. Application Data

(60) Provisional application No. 60/528,113, filed on Dec. 9, 2003.

(30) Foreign Application Priority Data

Nov. 19, 2003    (EP) .................................... 03104280

(51) Int. Cl.
*C12N 15/82*    (2006.01)
*C12N 5/04*    (2006.01)
*A01H 5/00*    (2006.01)
*A01H 5/10*    (2006.01)

(52) U.S. Cl. ..... 800/278; 800/287; 800/298; 800/320.3; 435/320.1; 435/419

(58) Field of Classification Search ....................... None
See application file for complete search history.

(56) References Cited

U.S. PATENT DOCUMENTS

| | | | | |
|---|---|---|---|---|
| 6,239,332 B1 * | 5/2001 | Ko et al. | ....................... | 800/290 |
| 2005/0221290 A1 * | 10/2005 | Inze et al. | ....................... | 435/5 |

OTHER PUBLICATIONS

Merriam Webster Online Dictionary. 2008, www.m-w.com/home.html.*
Bowie et al, Science 247:1306-1310, 1990.*
McConnell et al, Nature 411 (6838):709-713, 2001.*
Kano-Murakami et al (1993, FEBS 334:365-368).*

\* cited by examiner

*Primary Examiner* — Stuart F. Baum
(74) *Attorney, Agent, or Firm* — Barbara E. Johnson, Esq.

(57) ABSTRACT

The present invention concerns a method for modifying the growth characteristics of a plant relative to corresponding wild type plants, comprising modifying expression in a plant of a seedy1 nucleic acid and/or modifying the level and/or activity in a plant of a seedy1 protein. The invention also concerns novel constructs and novel seedy1 nucleic acid and protein sequences.

10 Claims, 10 Drawing Sheets

```
                                         1         Motif 1              40
                    CDS0689     (1)   ----MSVLQYPEGIDPADVQIWNNAAFDNGSEDLSPIKR
                    CDS0689 At  (1)   ---MTSIEATETLNAPPKEQIWNNAAFDDGDSQIISAIEA
         CDS0689 Medicago truncatula (1) ---MNNTNNNNILLHSTQVQIWNNAAFLGEDFAMNSSSDS
                    CDS0689 Os  (1)   ---------MEEDPLIPLVHVINNAAFDDSSCSRSAWIPQ
              CDS0689 Ta variant (1)  ---------MMEEDPLIPLVHVITHAFISSSSSSAWHAHA
                    CDS0689 So  (1)   ---------MEEDPLIPLVHVINNAAFDHASSSAWHAHSP
           CDS0689 Zm variantrev (1)  ---------MEEDPLIQLVHVINSNACDNAAASSVCHAH
              CDS0689 So variant (1)  ---------MEEDPLIPLVHVINNAPFDHASYSAWHAHSP
                    CDS0689 Bn est1 (1) ----MTSTEHTETLNAPEEQIWNNAAFDDGDSNLISAIEA
         CDS0689 Eschscholzia californica (1) ------MLEISETLNIPDIQIWNNAAFISGSTDNHTTAIK
                   CDS0689 Ga est1 (1) ----MSILQYPDSFNVPELQVWNNAAFDNGDSEDINAIKD
                    CDS0689 Pt  (1)   ---MSSILQYPDVVDAPEVQIWNNAAFINGSEGSLNIKS
            CDS0689 Plumbao zeylanica (1) MNEVLHIQEAARTDSSTIHQIWNNAAFISGSEDSPVVID
              CDS0689 Citrus sinensis (1) ----MSVLQYPITLNGQEIQIWNNAAFINGSEDSTAMKG
                    Consensus   (1)         I      E    IPEVQIWNNAAFD GDS  S  AI 41        Motif 2              80
                    CDS0689    (37)   --SWSPLKPLSVRPSDSFESDLSSIENQTILFENSSVNLS
                    CDS0689 At (38)   SSWSHLN-------ESFDSICS--ENQFFISVSSSLQSS
         CDS0689 Medicago truncatula (38) ------------------------IEVLNPSAFN------
                    CDS0689 Os (32)   ---SP--------AVAAVRKIDENHRIEVVD------
              CDS0689 Ta variant (33) ------------------TPVRRIEITRRIAETN------
                    CDS0689 So (32)   -----------VPASIRRIAIEIDIENHRIDPDP------
           CDS0689 Zm variantrev (32) -----------SPAPASAREGIGDINLRIEPDV------
              CDS0689 So variant (32) -----------ARASIGHEAIGDINHRIDPDP------
                    CDS0689 Bn est1 (37) ---------SWSNLNASFDSDCSIIQINVSVSSSLKSS
         CDS0689 Eschscholzia californica (35) ASSSPLKPIVLNQSEPSILDSIYTIIQTISCCISPVRTK
                   CDS0689 Ga est1 (37) SWCNFNS-----GSVNQSLESDGSIIQSILWIKSPVSFK
                    CDS0689 Pt (38)   -----------SWWNQSLIESDASIILSIVCEQSSPVFV
            CDS0689 Plumbao zeylanica (41) --F------SAPNLSQILLSDSSIIILSISLAEMPHPAK
              CDS0689 Citrus sinensis (37) SWANLKS-----VYMNQSLISSICSIILSIRLNKSPTSSL
                    Consensus  (41)                S  ESDG KEN P     S 81                              120
                    CDS0689    (75)   SPLPIKPLNPNGALENSRLKPNKPNSKQSLDEMAARKSGK
                    CDS0689 At (69)   VSITEAPS--------------AKSKTVKTKSAADRSKK-
         CDS0689 Medicago truncatula (49) ---IVPS-----------------------------SNK-
                    CDS0689 Os (53)   ---VAAG---------------------------------
              CDS0689 Ta variant (50) ----------------------------------------
                    CDS0689 So (54)   ----------------------------------------
           CDS0689 Zm variantrev (55) ----------------------------------------
              CDS0689 So variant (54) ----------------------------------------
                    CDS0689 Bn est1 (67) VSFSTDDP---------------IRCGKVK-----EKPH
         CDS0689 Eschscholzia californica (75) SPLPIKPLHPNG---------------------------
                   CDS0689 Ga est1 (72) STASVVKP-------LSSKNVTGNTREPFSAKMKSGVCKE
                    CDS0689 Pt (66)   NSSKPAKPLQ-----------------------------
            CDS0689 Plumbao zeylanica (73) SPMQK----------------------------------
              CDS0689 Citrus sinensis (72) KSCVPNKPLQVN----------SSVKNSQMKQLK--SVSK
                    Consensus  (81)
                                         121       Motif 3: coiled coil   160
                    CDS0689   (115)   GNDFRDEKKIDEEIEEIQMEISRLSSRLEALRIEKAEKTV
                    CDS0689 At (94)   --------RDIDAEIEEVEKEIGRLSIKLESLRIEKAEQTA
         CDS0689 Medicago truncatula (56) --------RTIDDEIAEIESEIKRLISKLELLRVEKAERKI
                    CDS0689 Os (57)   --------YDVEAEIGHIEAEILRLSSRLHHLRVSKQPEPN
              CDS0689 Ta variant (50) --------DADAEIARIEAEILRLSSRLHHLRVSKGHDAK
                    CDS0689 So (54)   --------DVEAEIGHIEAEILRLXSRLHHLRTSKQSEPS
           CDS0689 Zm variantrev (55) ---------EEMRHIEAEILRLSLRLHHLRTSQQLQPP
              CDS0689 So variant (54) --------DVEAEIGHIEAEILRLSSRLHHLRTSKQSEPP
                    CDS0689 Bn est1 (86) KTGKVRHGDIDAEIEEVEKFINRLSIRLESLRIEKAEQIA
         CDS0689 Eschscholzia californica (87) ----------------------------------------
                   CDS0689 Ga est1 (105) EEKKRDEKKIDMEIEEIEKEVARLSAKLESLRIEKPNIMQ
                    CDS0689 Pt (76)   ----------------------------------------
            CDS0689 Plumbao zeylanica (78) ----------------------------------------
              CDS0689 Citrus sinensis (100) EEETRDERKIDIEIEEIEKEISRLSSRLEALRIEKIDIKT
                    Consensus (121)          ID EI   IE EI RLSSRL  LRL  K
```

FIGURE 3

```
                                        401                                    440
                     CDS0689   (339)  IQSSVVRKRSLPENDKDESKRNDKKRSLSVGKTRVSQTES
                  CDS0689 At   (294)  TGEKDVRKRSLPEDEEKENHKRSEKR------RASDESN
      CDS0689 Medicago truncatula (284) GGD--ARKRSFSEN------------------------N
                  CDS0689 Os   (297)  AAAAATAKRMAGSSKMRVIPSRYSITPGESLSSSGAQERR
           CDS0689 Hv contig 123 (111) ISTASTCRRPAGSSKVVVPSRYSIMPGASLG-AATQDGR
              CDS0689 Ta contig (1)   ------------------GRYSLMPGASLGAASQERRR
            CDS0689 Zm partial  (87)  TSNVATTKRPAGSSKVIVVPSRYSIPPGSSIAAVTQGNRC
            CDS0689 Sacc sp 3'  (84)  TSNAATAKRPAGSSKVRVVPSRYSITPGYYLAAVSQDKRS
         CDS0689 Pinus taeda 3' (1)   ----------------------------------------
                   Consensus  (401)       KR        R    RYSL PGA LG
                                        441                                    480
                     CDS0689   (379)  KNL---GRESRVKKRWEIPSEIVVHGNTESEKSPLSIIVK
                  CDS0689 At   (327)  K------SEGRVKKRWEIPSEVDLYSSGEN--GDESPIVK
      CDS0689 Medicago truncatula (297) KGL---GSEIRAKKRWEIPIEEVDVSG-------FVM--
                  CDS0689 Os   (337)  RKQSLPGSSGDANQNEEIRAKVIEPSN--DPLSPQTISKV
           CDS0689 Hv contig 123 (150) RKESLPGSTGSTGQKEEIKAVPTEPVD--DDLSPESIDKV
              CDS0689 Ta contig (21)  KESLPGSIGGAGQKEEEIKAMPTEPVD--DDLSPESIDKV
            CDS0689 Zm partial  (127) KQS-----LPGSATETRVNLTEPPNDE----LSPERIAKV
            CDS0689 Sacc sp 3'  (124) KQS-LPGPASAASQREEIRAKLTEPSK--DELSPETVAKV
         CDS0689 Pinus taeda 3' (1)   -----------XEARIVFGTGNSAIMAGGTKAPDTLERH
                   Consensus  (441)   K     GS      REI A  E        LSPESL KV Motif 4
                                        481                                    520
                     CDS0689   (416)  PDLLPRIRIARCVNELLRDSSPAFRMIELIGKRSFFSSDE
                  CDS0689 At   (359)  --ELLKIRTQRRVGGSPRDSGAAKVAELQAK--------
      CDS0689 Medicago truncatula (324) ---LPKISTMRFVDESPRDSGAVKRVAELNGKRSXFCDED
                  CDS0689 Os   (375)  AEMLPKIRTMPPPDESPRDSGCAKRVAELVGKRSFFTAAA
           CDS0689 Hv contig 123 (188) AELLPRIRTMRPNEIPRDSGCAKRAADLVGKRSFFAAAA
              CDS0689 Ta contig (59)  AELLPRIRTMPPPDESPRDSGCAKRAADLVGKRSFFAIAA
            CDS0689 Zm partial  (158) AELLPRIRTMPPSDESPRDSGCAKKVADLVGKRSFFTAAG
            CDS0689 Sacc sp 3'  (161) AELLPRIKTMPASDESPRDSGCAKRVADLVGKRSFFTXAA
         CDS0689 Pinus taeda 3' (29)  KMKLEKIKTVRFTTESPRDSGCIEEIDRIGKSFFAPDG
                   Consensus  (481)   AELLPRIRTMP  DESPRDSGCAKRVADLVGKRSFF AAA
                                        521                                    560
                     CDS0689   (456)  --------DKEPPVCQVLSFAEEDAEEE-----------
                  CDS0689 At   (389)  --------DRNFTFCQILKFEE-----------------
      CDS0689 Medicago truncatula (361) EEERVMVEEEGGSVCQVLNFAEDDDDDDYGEQG------
                  CDS0689 Os   (415)  -----------EDGRALDVEAPEAVAEA-----------
           CDS0689 Hv contig 123 (228) AGD---GSAISSYQARVLEAPAPEEAAAAGALSDEAAAAG
              CDS0689 Ta contig (99)  AGD---CSAISSYQARVLEAPAPEEAAAAAEALGDEAASA
            CDS0689 Zm partial  (198) DDG----NLVTPYQARVVELESPEAAAEEAEA--------
            CDS0689 Sacc sp 3'  (201) EDG----NFVTPYQAPVGLL-------------------
         CDS0689 Pinus taeda 3' (69)  ITST--PSIDXXDAGEPLRRESVHEIXHAXXX--------
                   Consensus  (521)                    ARVLE EA E
                                        561              592
                     CDS0689   (476)  --------------------------------
                  CDS0689 At   (403)  --------------------------------
      CDS0689 Medicago truncatula (395) --------------------------------
                  CDS0689 Os   (432)  --------------------------------
           CDS0689 Hv contig 123 (265) ALSDEAAAAAAAAEALSDEAAAAEALSDEAAA
              CDS0689 Ta contig (136) GEALGDEAAA----------------------
            CDS0689 Zm partial  (226) --------------------------------
            CDS0689 Sacc sp 3'  (217) --------------------------------
         CDS0689 Pinus taeda 3' (99)  --------------------------------
                   Consensus  (561)
```

FIGURE 3 (continued)

SEQ ID NO 1: *Nicotiana tabacum* seedy1 coding sequence (CDS0689)

atgagtgtgttacaatacccagaagggattgacccagcagatgttcagatatggaacaatgc
agcatttgataatggagattctgaagatttgtcttcgctgaaacgttcttggtctcctctga
aaccccctttcggttaggccatcagattcctttgaatctgatttgtcaagtaaggaaaatcaa
actcctttatttgagaattcatctgttaatctctcatctccgttacccataaagccacttaa
ccctaatggggctctggaaaattcaagactcaagccgaacaagcccaattccaaacagagtc
ttgatgagatggcggctagaaagagcggaagggaaatgatttccgtgatgagaagaaaata
gacgaggaaattgaagaaattcagatggagattagtaggttgagttcaagattagaggcttt
gagaattgaaaaggctgagaaactgttgctaagactgttgaaaagcgaggaagggttgtgg
cagcaaagtttatggagccaaaacaaagtgttattaagattgaagagcgtatatcaatgagt
gcaagaacaaaggtggagcagagaagggggtcttagtttaggaccatctgagattttactgg
aacgcggcggcgagggttgagtatggggccatcagatattctagcagggacaacaaaggcac
ggcaattgggaaagcaagagatgattattactcctattcagccaatacaaacaggcgaaag
tcgtgtttttggaagcttcaagagattgaagaagagggaaaaagttcaagccttagtcctaa
atcaagaaaaactgctgcaagaacaatggttacaacaaggcaggcagttactacaattgcat
caaagaagaatttgaaaaagatgatggacttttgagttcagttcagccaagaagttgttt
aaagatctcgaaaagtctgctgctgctaataagaagccccagaggccggggagggttgtggc
tagtaggtataatcagagtacaattcagtcatcagtagtgagaagaggtctttacctgaaa
atgataaggatgagagtaagagaaatgataagaaacggtcgttatctgtagggaaaacgcgt
gtgtctcaaactgagagcaagaatttgggtactgaaagtagggtgaaaaagagatgggaaat
tcctagtgagattgtagttcatggaaacacagagagtgagaaatctccactaagcattattg
tgaagcctgatttgcttccgcgaattaggattgctcggtgtgtgaatgagactcttagggat
tctggacctgctaaaagaatgatagagttgataggcaagaaatcgttttcagtagtgatga
agataaggagccacctgtctgtcaagttttaagttttgcagaggaagatgctgaagaggaa**t
aa**

SEQ ID NO 2: *Nicotiana tabacum* seedy1 protein (CDS0689)
MSVLQYPEGIDPADVQIWNNAAFDNGDSEDLSSLKRSWSPLKPLSVRPSDSFESDLSSKENQ
TPLFENSSVNLSSPLPIKPLNPNGALENSRLKPNKPNSKQSLDEMAARKSGKGNDFRDEKKI
DEEIEEIQMEISRLSSRLEALRIEKAEKTVAKTVEKRGRVVAAKFMEPKQSVIKIEERISMS
ARTKVEQRRGLSLGPSEIFTGTRRRGLSMGPSDILAGTTKARQLGKQEMIITPIQPIQNRRK
SCFWKLQEIEEEGKSSSLSPKSRKTAARTMVTTRQAVTTIASKKNLKKDDGLLSSVQPKKLF
KDLEKSAAANKKPQRPGRVVASRYNQSTIQSSVVRKRSLPENDKDESKRNDKKRSLVGKTR
VSQTESKNLGTESRVKKRWEIPSEIVVHGNTESEKSPLSIIVKPDLLPRIRIARCVNETLRD
SGPAKRMIELIGKKSFFSSDEDKEPPVCQVLSFAEEDAEEE

FIGURE 4

**SEQ ID NO 3: *Oryza sativa* seedy1 coding sequence**
atggaggaggacccgctcatcccgctggtccacgtctggaacaacgccgccttcgacgactc
ctcgtgttccagatcggcttggctcccccaaagcccgccgtcgcggccgtccgcaagggcg
acaaggagaatcaccgccccgaggttgttgatgtcgccgccggctacgacgtcgaggccgag
atcggccacatcgaggcggagatcctgcgcctctcgtcccggctccaccatctccgcgtctc
caagcagccggagcccaaccgcgacgacgctccgatgggggagatggtcgcgaaggtgaggc
cccggccgagggcctcagcctcgggcccctggatgtgatctccatcgtcaatcgtgagaag
catccgctgcgcaccaagcagcctccggcgacgcggggcaggggctcagcctcgggcccat
ggagatcgccgcggcgaaccctagggtgcccgcggcggcgcagcatcagcaacagcaacgcg
ctggcacggcgcggatcctgaagccaatcaaggagcctccggtgcagcgtcgcagggcgtc
agcctcgggccgttggagatccaccacggcgtcggcagcaaggcaccagcggcggcgcgagc
caagccgttcaccaccaagctcaacgccattcgagaagaaacccgaccctccaagcaattcg
ccgtccccgccaagccatggccgtcgagcaatacaaggcagacactggactcgaggcaagga
acagcagcaagtcgagcgaaggcgaggagcccgagccccaggcccaggaggcaatccaatgg
caaggctactgacacaaggggaggcaacaaggtggtggatgagctcaagcccaaggtgcgt
cgtcaagtcagagcggcagcgccgccgccgccgccactgccaagaggatggcggggagctcc
aagatgagggtcatcccgagccgctacagcctcactcctggcgcttccttggaagcagtgg
agcacaggagaggcgacgcaagcagtctctcccaggatcatcaggggatgcgaaccagaatg
aggaaatcagagcgaaggtcatcgagccttccaatgatccactctctcctcaaacgatctcc
aaggttgctgaaatgctcccaaagatcaggaccatgccgcctcctgacgagagccctcgcga
ttccggatgcgccaagcgggttgccgaattggtcgggaagcgctcgttcttcacggctgcag
ccgaggacgggcgggcgctcgacgtcgaagcacccgaggcggtcgcagaagcttgagatgaa
ccaccatggtttgatccgttccttccatcagctc

**SEQ ID NO 4: *Oryza sativa* seedy1 protein**
MEEDPLIPLVHVWNNAAFDDSSCSRSAWLPQSPAVAAVRKGDKENHRPEVVDVAAGYDVEAE
IGHIEAEILRLSSRLHHLRVSKQPEPNRDDAPMGEMVAKVRPRPRGLSLGPLDVISIVNREK
HPLRTKQPPATRGRGLSLGPMEIAAANPRVPAAAQHQQQQRAGTARILKPIKEPPVQRRRGV
SLGPLEIHHGVGSKAPAAARAKPFTTKLNAIREETRPSKQFAVPAKPWPSSNTRQTLDSRQG
TAASRAKARSPSPRPRRQSNGKATDTRGGNKVVDELKPKGASSSQSGSAAAAATAKRMAGSS
KMRVIPSRYSLTPGASLGSSGAQERRRKQSLPGSSGDANQNEEIRAKVIEPSNDPLSPQTIS
KVAEMLPKIRTMPPPDESPRDSGCAKRVAELVGKRSFFTAAAEDGRALDVEAPEAVAEA

FIGURE 4 (continued)

**SEQ ID NO 5: *Medicago trunculata* seedy1 encoding sequence**
aaaaacgttaaggactaaaaatataataaaatttaagtagggattcataatggaagcacccc
tatttacagggatcttaaatataattaaccctaatatttatgacagaaacccttttgaaatc
acatcggagcgtgtatgagtagccgtttcacatccaacggccagtaagagcgtaactttatt
tcttccctcttcaatctccaacggtcacataatctcttccaaatacaaataattccctcttt
caacctcactcttcatttcttcaacccaaacccaaaaaactaatcagattcttcttaaatct
tgaaacctttctcccaaaagcacttaaataaaaagcacttaaccatgaataacacaaacaa
caacaacattcttcttcattccacacaggttcaagtgtggaacaacgcagcattcgatggtg
aagatttcgccatgaattcatcttctgattccatcaaagagaatctaaacccatccgcattc
aacattgttccttcttcaaacaaaagaactattgatgatgaaattgcggaaattgaaagtga
aattaagcgattaacttcgaagctggaattgcttcgtgttgaaaaagctgaaagaaaaatcg
cttctgaaagcgtgttagtggaattggtactggaagaatagtagcagcgaagtttatggaa
ccgaagaaaacgttacaccgaaacgaaacggtgtcgttttcaaggaggagacaccgaaacg
aaacggtgtcgtttcggatacgccgaaatctagggttaattggagaagagggatgagtttag
gtccgatggagattgccgggaaagtgatggcaccgccggcgatgacgattactccggcgacg
gtgaatcggaggaagtcttgtttctggaaaccgcaggaaagttgtgaagtaatgccgtcggg
gattactccggcgacggtgaataggaggaaatcttgttttttgaaacctcaagaaagttgtg
aagaaaatcgaagaaaaacgatttgcaaaccgaatttgaatttgaattcaaattcagttaat
tctgcggttggatcgattaagcgtgtgaagaagaaagatgaagaaattgctcaggttcaacc
gaagaagctgtttgaaggtgaaaaatcagtgaagaaatcgttgaaacaaggtagaattgttg
caagccggtataattccggtggtggtggtggtgatgcgaggaaaagatcgttttcggagaat
aataagggtttagggagtgaaatcagggctaagaagagatgggagataccaattgaagaagt
ggatgtgagtggttttgttatgttaccgaagatttcgacaatgaggtttgttgatgagagtc
ctagagattctggtgctgttaaaagagttgctgaattgatggaaaaagatcttactttgt
gatgaagatgaggaggagagagtgatggtggaggaagaaggtggttctgtttgtcaggtttt
gaattttgctgaagatgatgatgatgatgatgattatggtgaacaagggtaattgtggaaat
tggaattgatttgtttttgtggggttgtgtggaactggctatgttctgcttgattcttttgc
attttggtgtgaaactaaagatgaggtgaaaagtttatgcttgttaaattggattggtttat
atgttttgaaataataacaacaagcatgtgtcttgcttaataattgtatattgttttgtttg
ttttataatgatatggatttaatttgtatacacaatataatatagtatgcattgagagagtt
tttcgttcagtattcattctgatttttagtgtttatctcattctagaagattgtattttgttg

**SEQ ID NO 6: *Medicago trunculata* seedy1 protein**
MNNTNNNNILLHSTQVQVWNNAAFDGEDFAMNSSSDSIKENLNPSAFNIVPSSNKRTIDDEI
AEIESEIKRLTSKLELLRVEKAERKIASEKRVSGIGTGRIVAAKFMEPKKNVTPKRNGVVFK
EETPKRNGVVSDTPKSRVNWRRGMSLGPMEIAGKVMAPPAMTITPATVNRRKSCFWKPQESC
EVMPSGITPATVNRRKSCFLKPQESCEENRRKTICKPNLNLNSNSVNSAVGSIKRVKKKDEE
IAQVQPKKLFEGEKSVKKSLKQGRIVASRYNSGGGGGDARKRSFSENNKGLGSEIRAKKRWE
IPIEEVDVSGFVMLPKISTMRFVDESPRDSGAVKRVAELNGKRSYFCDEDEEERVMVEEEGG
SVCQVLNFAEDDDDDDDYGEQG

FIGURE 4 (continued)

**SEQ ID NO 7: *Saccharum sp.* encoding sequence (partial 5' end)**
Cgcaccgcgagtttcgaaaaaccaacctatcgcgcctcagatcacgcgaggacgcgagggga
agcaggaatccctccgctcccagccgcctcctccgctcacccatcgatcgatcgtccgtccg
gtccagggggctctccggcggcggtggcgatggaggaggacccgctcatcccgctggtgcac
gtctggaacaacgccgccttcgaccacgcctcctcctccgcgtggcacgccactccctgt
gcccgcgagcgcacgtcgcgaggcggaggggacaaggagaaccaccgcccgaccccgacc
ccgacgtcgaggcggagatcggccacatcgaggcggagatcctgcgcctgtnctcccgcctn
caccaccttcgcacctccaagcagtcggagccgtccaagcgcggagaggtcgcgcccgcgcc
cgcggcgaaggcgaaagcggcggcggcggcgcggctgcggacgcggggctcagcctgggcc
cgctcgacgtcgccgctgccggtaaccccaacccgctcaccaccgacaaccagcagcagcag
ccgcgtgccgcgcagggtctgaagccgatcaagcaggccacggcggcggcgggcaagggcgt
aagacttgggccccttcgacatggtcggcgcgaaccctagggtccctccgcccn

**SEQ ID NO 8: *Saccharum sp.* seedy1 protein (partial N-term)**
MEEDPLIPLVHVWNNAAFDHASSSAWHAHSPVPASARREAEGDKENHRPDPDPDVEAEIGHI
EAEILRLXSRLHHLRTSKQSEPSKRGEVAPAPAAKAKAAAAARLRTRGLSLGPLDVAAAGNP
NPLTTDNQQQQPRAAQGLKPIKQATAAAGKGVRLGPLRHGRR

**SEQ ID NO 9: *Zea Mays* seedy1 encoding sequence (partial 3' end)**
ccacgcgtccggccgttcgagaggaggaaggccagcgttccaaggagcacgccgtccccgcc
agaccgtggccatccagcaatgccaggcacccactggatgccaggcaaggcaccgcagcaag
cagagccaaggcgaggagcgggagcataagccccagcaggttcaggaggcagtccacttcca
aggctgccgagacaagagcgggaaatgccaagcctacagaggcgacgagggagggagcgaa
gcggtcaatcacaccagcaatgtagccacgacgaagaggccggcggggagctccaaggtcag
ggttgtcccgagccgctacagcatcccacctggctcctccctagcagctgtgacacaaggca
accgatgcaagcagtctctcccaggatcggctactgagaccagagtaaatctcactgagccg
ccgaacgacgagttgtctcctgaagaacttgccaaggttgcagagctgctcccaaggattag
gaccatgccgccttctgatgagagcccgcgtgactcgggatgtgccaagcgtgttgctgatt
tggtcgggaagcgatccttcttcactgctgcaggggacgatggcaatctcgttacgccctac
caggcacgggtggttgaacttgaatcacccgaggcagcagcagaagaagcagaagcttgaga
agtttgtctttgatcaattccgaagtggcttgcatctgggcgtggcctcttttgcagtgtg
tgctactacatagtctactgttacattcatatcatatcacatttcctatttttccccttg
agacattgcttagtacttttgtgttgccttgtgaaaagagagtggaaggttcatctgctgat
nccttgtt

**SEQ ID NO 10: *Zea Mays* seedy1 protein (partial C-term)**
TRPAVREEEGQRSKEHAVPARPWPSSNARHPLDARQGTAASRAKARSGSISPSRFRRQSTSK
AAETRAGNAKPTEATRGGSEAVNHTSNVATTKRPAGSSKVRVVPSRYSIPPGSSLAAVTQGN
RCKQSLPGSATETRVNLTEPPNDELSPEELAKVAELLPRIRTMPPSDESPRDSGCAKRVADL
VGKRSFFTAAGDDGNLVTPYQARVVELESPEAAAEEAE

FIGURE 4 (continued)

**SEQ ID NO 11: *Arabidospis thaliana* seedy1 coding sequence**
atgacatcaattgaggcaacagaaacgcttaacgctcctccaaagcttcagatctggaacaa
cgctgccttcgacgatggagattctcaaatcacttccgccatcgaagcttcttcttggtctc
acctcaacgaatcattcgattccgattgtagcaaggagaatcagtttccgatttcggtttcc
tcttcgctccaatcctcagtctcgatcaccgaagctccgtcagcaaaatccaagaccgtgaa
gaccaaatccgccgcagatcggagtaaaaagcgagatatcgatgcagagatcgaagaagtag
agaaggagatcggacgattatcgacgaaattggagtcgctccgattagagaaggcggagcaa
accgcaagaagcattgctatacgtggaagaatcgttccggcgaagttcatggaatcatctca
gaaacaagtgaaattcgacgattcgtgttttacaggatcgaaatcaagagccactcgtagag
gcgttagtcttggaccagcggagatattcaattccgcgaagaaatctgaaactgtgactcct
cttcaatcagctcagaatcgacgcaagtcttgtttctttaagcttcctggaatcgaagaagg
tcaagtgacgacacgaggtaaaggaagaacgagtttgagtctgagtccgagatctcgcaaag
cgaaaatgacggcagctcagaagcaagcagctacgacggtggggtcaaagagagctgtgaag
aaagaagaaggagttctcttaacaatccagcctaagaggctattcaaagaagatgaaaagaa
tgtttctttaaggaaaccattgaaaccaggaagagttgtggctagtaggtacagtcaaatgg
gtaaaacgcagactggagagaaagatgttaggaaaaggtcgttgcctgaggatgaagagaaa
gagaatcataagaggtcggagaagagaagagcttctgatgaaagtaacaagagtgaagggag
agtgaagaagagatgggagattccaagtgaagttgatctgtatagcagtggtgagaacggtg
acgagtctcctatagttaaggagctacctaagatcagaacgcttcgtcgtgtgggagggagc
cctcgtgattcaggtgctgctaagagagttgcagaattacaagccaaggatcgtaacttcac
ttttgccagcttctgaagtttgaagaatgaatgatccgcttatcaatttgagtaaaatcca
caactcttgttgtggtt

**SEQ ID NO 12: *Arabidospis thaliana* seedy1 protein**
MTSIEATETLNAPPKLQIWNNAAFDDGDSQITSAIEASSWSHLNESFDSDCSKENQFPISVS
SSLQSSVSITEAPSAKSKTVKTKSAADRSKKRDIDAEIEEVEKEIGRLSTKLESLRLEKAEQ
TARSIAIRGRIVPAKFMESSQKQVKFDDSCFTGSKSRATRRGVSLGPAEIFNSAKKSETVTP
LQSAQNRRKSCFFKLPGIEEGQVTTRGKGRTSLSLSPRSRKAKMTAAQKQAATTVGSKRAVK
KEEGVLLTIQPKRLFKEDEKNVSLRKPLKPGRVVASRYSQMGKTQTGEKDVRKRSLPEDEEK
ENHKRSEKRRASDESNKSEGRVKKRWEIPSEVDLYSSGENGDESPIVKELPKIRTLRRVGGS
PRDSGAAKRVAELQAKDRNFTFCQLLKFEE

FIGURE 4 (continued)

SEQ ID NO 13: Sequence of the [PRO0090 – CDS0689 – terminator] expression cassette cttctacatcggcttaggtgtagcaacacgactttattattattattattattattatt
attttacaaaaatataaaatagatcagtccctcaccacaagtagagcaagttggtgagttat
tgtaaagttctacaaagctaatttaaaagttattgcattaacttatttcatattacaaacaa
gagtgtcaatggaacaatgaaaaccatatgacatactataattttgtttttattattgaaat
tatataattcaaagagaataaatccacatagccgtaaagttctacatgtggtgcattaccaa
aatatatatagcttacaaaacatgacaagcttagtttgaaaaattgcaatccttatcacatt
gacacataaagtgagtgatgagtcataatattattttctttgctacccatcatgtatatatg
atagccacaaagttactttgatgatgatatcaaagaacattttttaggtgcacctaacagaat
atccaataatatgactcacttagatcataatagagcatcaagtaaaactaacactctaaag
caaccgatgggaaagcatctataaatagacaagcacaatgaaaatcctcatcatccttcacc
acaattcaaatattatagttgaagcatagtagtaatttaaatcaactagggatatcacaagt
ttgtacaaaaaagcaggctggtaccggtccggaattcccgggatatcgtcgacccacgcgtc
cgctgacgcgtgggttccactacatcaagacatctactacactcatctttttgcacttatt
gggtgtaaattttgaaacccagttgagaaaaatgagtgtgttacaatacccagaagggatt
gacccagcagatgttcagatatggaacaatgcagcatttgataatggagattctgaagattt
gtcttcgctgaaacgttcttggtctcctctgaaaccctttcggttaggccatcagattcct
ttgaatctgatttgtcaagtaaggaaaatcaaactcctttatttgagaattcatctgttaat
ctctcatctccgttacccataaagccacttaacccctaatggggctctggaaaattcaagact
caagccgaacaagcccaattccaaacagagtcttgatgagatggcggctagaaagagcggaa
agggaaatgatttccgtgatgagaagaaaatagacgaggaaattgaagaaattcagatggag
attagtaggttgagttcaagattagaggctttgagaattgaaaaggctgagaaaactgttgc
taagactgttgaaaagcgaggaagggttgtggcagcaaagtttatggagccaaaacaaagtg
ttattaagattgaagagcgtatatcaatgagtgcaagaacaaaggtggagcagagaagggt
cttagtttaggaccatctgagattttactggaacgcggcggcgagggttgagtatggggcc
atcagatattctagcagggacaacaaaggcacggcaattgggaaagcaagagatgattata
ctcctattcagccaatacaaaacaggcgaaagtcgtgtttttggaagcttcaagagattgaa
gaagagggaaaaagttcaagccttagtcctaaatcaagaaaaactgctgcaagaacaatggt
tacaacaaggcaggcagttactacaattgcatcaaagaagaatttgaaaaagatgatggac
ttttgagttcagttcagccaaagaagttgtttaaagatctcgaaaagtctgctgctgctaat
aagaagccccagaggccggggagggttgtggctagtaggtataatcagagtacaattcagtc
atcagtagtgagaaagaggtctttacctgaaaatgataaggatgagagtaagagaaatgata
agaaacggtcgttatctgtagggaaaacgcgtgtgtctcaaactgagagcaagaatttgggt
actgaaagtagggtgaaaaagagatgggaaattcctagtgagattgtagttcatggaaacac
agagagtgagaaatctccactaagcattattgtgaagcctgatttgcttccgcgaattagga
ttgctcggtgtgtgaatgagactcttagggattctggacctgctaaaagaatgatagagttg
ataggcaagaaatcgttttcagtagtgatgaagataaggagccacctgtctgtcaagtttt
aagttttgcagaggaagatgctgaagaggaataatgtgtaataaagggagctgctaactctt
ttcatgctctttcaattttcaatcctgccttttaattttgttcattcgtgcctttaattg
aatggggaagcattcttttgcttcctcaaactggtattctagcttctgaattacattgtatg
gtacaatatgaataaggttttgtcttccggcaggttgtccaagttagttttagcttaaaat
agatgcggcagcggccgctctagagtatccctcgaggggcccaagcttacgcgtacccagct

FIGURE 4 (continued)

```
ttcttgtacaaagtggtgatatcacaagcccgggcggtcttctagggataacagggtaatta
tatccctctagatcacaagcccgggcggtcttctacgatgattgagtaataatgtgtcacgc
atcaccatgggtggcagtgtcagtgtgagcaatgacctgaatgaacaattgaaatgaaaaga
aaaaagtactccatctgttccaaattaaaattcatttttaacctttaataggtttatacaa
taattgatatatgttttctgtatatgtctaatttgttatcatccgggcggtcttctagggat
aacagggtaattatatccctctagacaacacacaacaaataagagaaaaaacaaataatatt
aatttgagaatgaacaaaaggaccatatcattcattaactcttctccatccatttccatttc
acagttcgatagcgaaaaccgaataaaaaacacagtaaattacaagcacaacaaatggtaca
agaaaaacagttttcccaatgccataatactcgaac
```

SEQ ID NO 14: rice prolamin RP6 promoter sequence
```
ccttctacatcggcttaggtgtagcaacacgactttattattattattattattattattat
tattttacaaaaatataaaatagatcagtccctcaccacaagtagagcaagttggtgagtta
ttgtaaagttctacaaagctaatttaaaagttattgcattaacttatttcatattacaaaca
agagtgtcaatggaacaatgaaaaccatatgacatactataattttgttttttattattgaaa
ttatataattcaaagagaataaatccacatagccgtaaagttctacatgtggtgcattacca
aaatatatatagcttacaaaacatgacaagcttagtttgaaaaattgcaatccttatcacat
tgacacataaagtgagtgatgagtcataatattattttttcttgctacccatcatgtatatat
gatagccacaaagttactttgatgatgatatcaaagaacatttttaggtgcacctaacagaa
tatccaaataatatgactcacttagatcataatagagcatcaagtaaaactaacactctaaa
gcaaccgatgggaaagcatctataaatagacaagcacaatgaaaatcctcatcatccttcac
cacaattcaaatattatagttgaagcatagtagtagaatccaacaaca
```

SEQ ID NO 35: Motif 1 CORE SEQUENCE
WXNAXXD

SEQ ID NO 16: Motif 2 CORE SEQUENCE
KENXXP

SEQ ID NO 36: Motif 3 (coiled coil) CORE SEQUENCE
$EX_{1-6}EXXRLXXXLXXLR$

SEQ ID NO 37: Motif 4 CORE SEQUENCE
$LPXIX_{1-10}RDSGXXKRX_{1-6}K$

SEQUENCE LISTING

<160> NUMBER OF SEQ ID NOS: 37

<210> SEQ ID NO 1
<211> LENGTH: 1428
<212> TYPE: DNA
<213> ORGANISM: Nicotiana tabacum
<220> FEATURE:
<223> OTHER INFORMATION: Seedy1 coding sequence (CDS0689)

<400> SEQUENCE: 1

```
atgagtgtgt tacaataccc agaagggatt gacccagcag atgttcagat atggaacaat       60
gcagcatttg ataatggaga ttctgaagat ttgtcttcgc tgaaacgttc ttggtctcct      120
ctgaaacccc tttcggttag gccatcagat tcctttgaat ctgatttgtc aagtaaggaa      180
aatcaaactc ctttatttga gaattcatct gttaatctct catctccgtt acccataaag      240
ccacttaacc ctaatggggc tctggaaaat tcaagactca agccgaacaa gcccaattcc      300
aaacagagtc ttgatgagat ggcggctaga aagagcggaa agggaaatga tttccgtgat      360
gagaagaaaa tagacgagga aattgaagaa attcagatgg agattagtag gttgagttca      420
agattagagg ctttgagaat tgaaaaggct gagaaaactg ttgctaagac tgttgaaaag      480
cgaggaaggg ttgtggcagc aaagtttatg gagccaaaac aaagtgttat taagattgaa      540
gagcgtatat caatgagtgc aagaacaaag gtggagcaga aaggggtct tagtttagga       600
ccatctgaga ttttttactgg aacgcggcgg cgagggttga gtatgggggcc atcagatatt      660
ctagcaggga caacaaaggc acggcaattg ggaaagcaag agatgattat tactcctatt      720
cagccaatac aaaacaggcg aaagtcgtgt ttttggaagc ttcaagagat tgaagaagag      780
ggaaaaagtt caagccttag tcctaaatca agaaaaactg ctgcaagaac aatggttaca      840
acaaggcagg cagttactac aattgcatca agaagaatt tgaaaaaaga tgatggactt      900
ttgagttcag ttcagccaaa gaagttgttt aaagatctcg aaaagtctgc tgctgctaat      960
aagaagcccc agaggccggg gagggttgtg gctagtaggt ataatcagag tacaattcag     1020
tcatcagtag tgagaaagag gtctttacct gaaaatgata aggatgagag taagagaaat     1080
gataagaaac ggtcgttatc tgtagggaaa acgcgtgtgt ctcaaactga gagcaagaat     1140
ttgggtactg aaagtagggt gaaaaagaga tgggaaattc ctagtgagat tgtagttcat     1200
ggaaacacag agagtgagaa atctccacta agcattattg tgaagcctga tttgcttccg     1260
cgaattagga ttgctcggtg tgtgaatgag actcttaggg attctggacc tgctaaaaga     1320
atgatagagt tgataggcaa gaaatcgttt tcagtagtg atgaagataa ggagccacct     1380
gtctgtcaag ttttaagttt tgcagaggaa gatgctgaag aggaataa               1428
```

<210> SEQ ID NO 2

<211> LENGTH: 475
<212> TYPE: PRT
<213> ORGANISM: Nicotiana tabacum
<220> FEATURE:
<223> OTHER INFORMATION: Seedy1 protein (CDS0689)

<400> SEQUENCE: 2

| | | | | | | | | | | | | | | |
|---|---|---|---|---|---|---|---|---|---|---|---|---|---|---|
| Met | Ser | Val | Leu | Gln | Tyr | Pro | Glu | Gly | Ile | Asp | Pro | Ala | Asp | Val | Gln |
| 1 | | | | 5 | | | | | 10 | | | | | 15 | |

| Ile | Trp | Asn | Asn | Ala | Ala | Phe | Asp | Asn | Gly | Asp | Ser | Glu | Asp | Leu | Ser |
|---|---|---|---|---|---|---|---|---|---|---|---|---|---|---|---|
| | | | 20 | | | | | 25 | | | | | 30 | | |

| Ser | Leu | Lys | Arg | Ser | Trp | Ser | Pro | Leu | Lys | Pro | Leu | Ser | Val | Arg | Pro |
|---|---|---|---|---|---|---|---|---|---|---|---|---|---|---|---|
| | | | 35 | | | | | 40 | | | | | 45 | | |

| Ser | Asp | Ser | Phe | Glu | Ser | Asp | Leu | Ser | Ser | Lys | Glu | Asn | Gln | Thr | Pro |
|---|---|---|---|---|---|---|---|---|---|---|---|---|---|---|---|
| | 50 | | | | | 55 | | | | | 60 | | | | |

| Leu | Phe | Glu | Asn | Ser | Ser | Val | Asn | Leu | Ser | Ser | Pro | Leu | Pro | Ile | Lys |
|---|---|---|---|---|---|---|---|---|---|---|---|---|---|---|---|
| 65 | | | | | 70 | | | | | 75 | | | | | 80 |

| Pro | Leu | Asn | Pro | Asn | Gly | Ala | Leu | Glu | Asn | Ser | Arg | Leu | Lys | Pro | Asn |
|---|---|---|---|---|---|---|---|---|---|---|---|---|---|---|---|
| | | | | 85 | | | | | 90 | | | | | 95 | |

| Lys | Pro | Asn | Ser | Lys | Gln | Ser | Leu | Asp | Glu | Met | Ala | Ala | Arg | Lys | Ser |
|---|---|---|---|---|---|---|---|---|---|---|---|---|---|---|---|
| | | | 100 | | | | | 105 | | | | | 110 | | |

| Gly | Lys | Gly | Asn | Asp | Phe | Arg | Asp | Glu | Lys | Lys | Ile | Asp | Glu | Glu | Ile |
|---|---|---|---|---|---|---|---|---|---|---|---|---|---|---|---|
| | | | 115 | | | | | 120 | | | | | 125 | | |

| Glu | Glu | Ile | Gln | Met | Glu | Ile | Ser | Arg | Leu | Ser | Ser | Arg | Leu | Glu | Ala |
|---|---|---|---|---|---|---|---|---|---|---|---|---|---|---|---|
| | 130 | | | | | 135 | | | | | 140 | | | | |

| Leu | Arg | Ile | Glu | Lys | Ala | Glu | Lys | Thr | Val | Ala | Lys | Thr | Val | Glu | Lys |
|---|---|---|---|---|---|---|---|---|---|---|---|---|---|---|---|
| 145 | | | | | 150 | | | | | 155 | | | | | 160 |

| Arg | Gly | Arg | Val | Val | Ala | Ala | Lys | Phe | Met | Glu | Pro | Lys | Gln | Ser | Val |
|---|---|---|---|---|---|---|---|---|---|---|---|---|---|---|---|
| | | | | 165 | | | | | 170 | | | | | 175 | |

| Ile | Lys | Ile | Glu | Glu | Arg | Ile | Ser | Met | Ser | Ala | Arg | Thr | Lys | Val | Glu |
|---|---|---|---|---|---|---|---|---|---|---|---|---|---|---|---|
| | | | 180 | | | | | 185 | | | | | 190 | | |

| Gln | Arg | Arg | Gly | Leu | Ser | Leu | Gly | Pro | Ser | Glu | Ile | Phe | Thr | Gly | Thr |
|---|---|---|---|---|---|---|---|---|---|---|---|---|---|---|---|
| | | | 195 | | | | | 200 | | | | | 205 | | |

| Arg | Arg | Arg | Gly | Leu | Ser | Met | Gly | Pro | Ser | Asp | Ile | Leu | Ala | Gly | Thr |
|---|---|---|---|---|---|---|---|---|---|---|---|---|---|---|---|
| | 210 | | | | | 215 | | | | | 220 | | | | |

| Thr | Lys | Ala | Arg | Gln | Leu | Gly | Lys | Gln | Glu | Met | Ile | Ile | Thr | Pro | Ile |
|---|---|---|---|---|---|---|---|---|---|---|---|---|---|---|---|
| 225 | | | | | 230 | | | | | 235 | | | | | 240 |

| Gln | Pro | Ile | Gln | Asn | Arg | Arg | Lys | Ser | Cys | Phe | Trp | Lys | Leu | Gln | Glu |
|---|---|---|---|---|---|---|---|---|---|---|---|---|---|---|---|
| | | | | 245 | | | | | 250 | | | | | 255 | |

| Ile | Glu | Glu | Glu | Gly | Lys | Ser | Ser | Leu | Ser | Pro | Lys | Ser | Arg | Lys |
|---|---|---|---|---|---|---|---|---|---|---|---|---|---|---|
| | | | 260 | | | | | 265 | | | | | 270 | |

| Thr | Ala | Ala | Arg | Thr | Met | Val | Thr | Thr | Arg | Gln | Ala | Val | Thr | Thr | Ile |
|---|---|---|---|---|---|---|---|---|---|---|---|---|---|---|---|
| | | | 275 | | | | | 280 | | | | | 285 | | |

| Ala | Ser | Lys | Lys | Asn | Leu | Lys | Lys | Asp | Asp | Gly | Leu | Leu | Ser | Ser | Val |
|---|---|---|---|---|---|---|---|---|---|---|---|---|---|---|---|
| | 290 | | | | | 295 | | | | | 300 | | | | |

| Gln | Pro | Lys | Lys | Leu | Phe | Lys | Asp | Leu | Glu | Lys | Ser | Ala | Ala | Ala | Asn |
|---|---|---|---|---|---|---|---|---|---|---|---|---|---|---|---|
| 305 | | | | | 310 | | | | | 315 | | | | | 320 |

| Lys | Lys | Pro | Gln | Arg | Pro | Gly | Arg | Val | Val | Ala | Ser | Arg | Tyr | Asn | Gln |
|---|---|---|---|---|---|---|---|---|---|---|---|---|---|---|---|
| | | | | 325 | | | | | 330 | | | | | 335 | |

| Ser | Thr | Ile | Gln | Ser | Ser | Val | Val | Arg | Lys | Arg | Ser | Leu | Pro | Glu | Asn |
|---|---|---|---|---|---|---|---|---|---|---|---|---|---|---|---|
| | | | 340 | | | | | 345 | | | | | 350 | | |

| Asp | Lys | Asp | Glu | Ser | Lys | Arg | Asn | Asp | Lys | Lys | Arg | Ser | Leu | Ser | Val |
|---|---|---|---|---|---|---|---|---|---|---|---|---|---|---|---|
| | | 355 | | | | | 360 | | | | | 365 | | | |

| Gly | Lys | Thr | Arg | Val | Ser | Gln | Thr | Glu | Ser | Lys | Asn | Leu | Gly | Thr | Glu |
|---|---|---|---|---|---|---|---|---|---|---|---|---|---|---|---|
| | 370 | | | | | 375 | | | | | 380 | | | | |

```
Ser Arg Val Lys Lys Arg Trp Glu Ile Pro Ser Glu Ile Val Val His
385                 390                 395                 400

Gly Asn Thr Glu Ser Glu Lys Ser Pro Leu Ser Ile Ile Val Lys Pro
                405                 410                 415

Asp Leu Leu Pro Arg Ile Arg Ile Ala Arg Cys Val Asn Glu Thr Leu
            420                 425                 430

Arg Asp Ser Gly Pro Ala Lys Arg Met Ile Glu Leu Ile Gly Lys Lys
        435                 440                 445

Ser Phe Phe Ser Ser Asp Glu Asp Lys Glu Pro Pro Val Cys Gln Val
    450                 455                 460

Leu Ser Phe Ala Glu Glu Asp Ala Glu Glu Glu
465                 470                 475

<210> SEQ ID NO 3
<211> LENGTH: 1336
<212> TYPE: DNA
<213> ORGANISM: Oryza sativa
<220> FEATURE:
<223> OTHER INFORMATION: Seedy1 coding sequence

<400> SEQUENCE: 3
atggaggagg acccgctcat cccgctggtc cacgtctgga caacgccgc cttcgacgac      60 tcctcgtgtt ccagatcggc ttggctcccc caaagccccg ccgtcgcggc cgtccgcaag     120
ggcgacaagg agaatcaccg ccccgaggtt gttgatgtcg ccgccggcta cgacgtcgag     180
gccgagatcg ccacacatcga gcggagatc ctgcgcctct cgtcccgct ccaccatctc      240 cgcgtctcca agcagccgga gcccaaccgc gacgacgctc cgatggggga gatggtcgcg     300
aaggtgaggc cccggccgag gggcctcagc ctcgggcccc tggatgtgat ctccatcgtc     360
aatcgtgaga gcatccgct cgcaccaag cagcctccgg cgacgcgggg caggggctc       420 agcctcgggc ccatggagat cgccgcggcg aaccctaggg tgcccgcggc ggcgcagcat     480
cagcaacagc aacgcgctgg cacggcgcgg atcctgaagc caatcaagga gcctccggtg     540
cagcgtcgca ggggcgtcag cctcgggccg ttggagatcc accacggcgt cggcagcaag     600
gcaccagcgg cggcgcgagc caagccgttc accaccaagc tcaacgccat cgagaagaa      660 acccgaccct ccaagcaatt cgccgtcccc gccaagccat ggcgtcgag caatacaagg      720 cagacactgg actcgaggca aggaacagca gcaagtcgag cgaaggcgag gagcccgagc     780
cccaggccca ggaggcaatc caatggcaag gctactgaca aaggggagg caacaaggtg      840 gtggatgagc tcaagcccaa aggtgcgtcg tcaagtcaga gcggcagcgc cgccgccgcc     900
gccactgcca agaggatggc ggggagctcc aagatgaggg tcatcccgag ccgctacagc     960
ctcactcctg gcgcttccct tggaagcagt ggagcacagg agaggcgacg caagcagtct    1020
ctcccaggat catcagggga tgcgaaccag aatgaggaaa tcagagcgaa ggtcatcgag    1080
ccttccaatg atccactctc tcctcaaacg atctccaagg ttgctgaaat gctcccaaag    1140
atcaggacca tgccgcctcc tgacgagagc cctcgcgatt ccggatgcgc caagcgggtt    1200
gccgaattgg tcgggaagcg ctcgttcttc acgctgcag ccgaggacgg gcgggcgctc     1260
gacgtcgaag cacccgaggc ggtcgcagaa gcttgagatg aaccaccatg gtttgatccg    1320
ttccttccat cagctc                                                    1336

<210> SEQ ID NO 4
<211> LENGTH: 431
<212> TYPE: PRT
<213> ORGANISM: Oryza sativa
<220> FEATURE:
```

<223> OTHER INFORMATION: Seedy1 protein

<400> SEQUENCE: 4

```
Met Glu Glu Asp Pro Leu Ile Pro Leu Val His Val Trp Asn Asn Ala
1               5                   10                  15

Ala Phe Asp Asp Ser Ser Cys Ser Arg Ser Ala Trp Leu Pro Gln Ser
            20                  25                  30

Pro Ala Val Ala Ala Val Arg Lys Gly Asp Lys Glu Asn His Arg Pro
        35                  40                  45

Glu Val Val Asp Val Ala Ala Gly Tyr Asp Val Glu Ala Glu Ile Gly
    50                  55                  60

His Ile Glu Ala Glu Ile Leu Arg Leu Ser Ser Arg Leu His His Leu
65                  70                  75                  80

Arg Val Ser Lys Gln Pro Glu Pro Asn Arg Asp Asp Ala Pro Met Gly
                85                  90                  95

Glu Met Val Ala Lys Val Arg Pro Arg Pro Arg Gly Leu Ser Leu Gly
            100                 105                 110

Pro Leu Asp Val Ile Ser Ile Val Asn Arg Glu Lys His Pro Leu Arg
        115                 120                 125

Thr Lys Gln Pro Pro Ala Thr Arg Gly Arg Gly Leu Ser Leu Gly Pro
130                 135                 140

Met Glu Ile Ala Ala Ala Asn Pro Arg Val Pro Ala Ala Ala Gln His
145                 150                 155                 160

Gln Gln Gln Gln Arg Ala Gly Thr Ala Arg Ile Leu Lys Pro Ile Lys
                165                 170                 175

Glu Pro Pro Val Gln Arg Arg Gly Val Ser Leu Gly Pro Leu Glu
            180                 185                 190

Ile His His Gly Val Gly Ser Lys Ala Pro Ala Ala Arg Ala Lys
        195                 200                 205

Pro Phe Thr Thr Lys Leu Asn Ala Ile Arg Glu Glu Thr Arg Pro Ser
    210                 215                 220

Lys Gln Phe Ala Val Pro Ala Lys Pro Trp Pro Ser Ser Asn Thr Arg
225                 230                 235                 240

Gln Thr Leu Asp Ser Arg Gln Gly Thr Ala Ala Ser Arg Ala Lys Ala
                245                 250                 255

Arg Ser Pro Ser Pro Arg Pro Arg Gln Ser Asn Gly Lys Ala Thr
            260                 265                 270

Asp Thr Arg Gly Gly Asn Lys Val Val Asp Glu Leu Lys Pro Lys Gly
        275                 280                 285

Ala Ser Ser Ser Gln Ser Gly Ser Ala Ala Ala Ala Thr Ala Lys
    290                 295                 300

Arg Met Ala Gly Ser Ser Lys Met Arg Val Ile Pro Ser Arg Tyr Ser
305                 310                 315                 320

Leu Thr Pro Gly Ala Ser Leu Gly Ser Ser Gly Ala Gln Glu Arg Arg
                325                 330                 335

Arg Lys Gln Ser Leu Pro Gly Ser Ser Gly Asp Ala Asn Gln Asn Glu
            340                 345                 350

Glu Ile Arg Ala Lys Val Ile Glu Pro Ser Asn Asp Pro Leu Ser Pro
        355                 360                 365

Gln Thr Ile Ser Lys Val Ala Glu Met Leu Pro Lys Ile Arg Thr Met
    370                 375                 380

Pro Pro Pro Asp Glu Ser Pro Arg Asp Ser Gly Cys Ala Lys Arg Val
385                 390                 395                 400

Ala Glu Leu Val Gly Lys Arg Ser Phe Phe Thr Ala Ala Ala Glu Asp
```

```
                    405                 410                 415
Gly Arg Ala Leu Asp Val Glu Ala Pro Glu Ala Val Ala Glu Ala
            420                 425                 430

<210> SEQ ID NO 5
<211> LENGTH: 1860
<212> TYPE: DNA
<213> ORGANISM: Medicago trunculata
<220> FEATURE:
<223> OTHER INFORMATION: Seedy1 coding sequence

<400> SEQUENCE: 5
aaaaacgtta aggactaaaa atataataaa atttaagtag ggattcataa tggaagcacc      60
cctatttaca gggatcttaa atataattaa ccctaatatt tatgacagaa acccttttga    120
aatcacatcg gagcgtgtat gagtagccgt ttcacatcca acggccagta agagcgtaac    180
tttatttctt ccctcttcaa tctccaacgg tcacataatc tcttccaaat acaataatt     240 ccctctttca acctcactct tcatttcttc aacccaaacc caaaaaacta atcagattct    300
tcttaaatct tgaaaccttt ctcccaaaag cacttaaata aaaagcact  taaccatgaa    360 taacacaaac aacaacaaca ttcttcttca ttccacacag gttcaagtgt ggaacaacgc    420
agcattcgat ggtgaagatt cgccatgaa ttcatcttct gattccatca agagaatct      480 aaacccatcc gcattcaaca ttgttccttc ttcaaacaaa gaactattg atgatgaaat     540 tgcggaaatt gaaagtgaaa ttaagcgatt aacttcgaag ctggaattgc ttcgtgttga    600
aaaagctgaa agaaaaatcg cttctgaaaa gcgtgttagt ggaattggta ctggaagaat    660
agtagcagcg aagtttatgg aaccgaagaa aaacgttaca ccgaaacgaa acggtgtcgt    720
tttcaaggag gagacaccga aacgaaacgg tgtcgtttcg gatacgccga aatctagggt    780
taattggaga gagggatga gtttaggtcc gatggagatt gccgggaaag tgatggcacc     840
gccggcgatg acgattactc cggcgacggt gaatcggagg aagtcttgtt tctggaaacc    900
gcaggaaagt tgtgaagtaa tgccgtcggg gattactccg gcgacggtga ataggaggaa    960
atcttgtttt ttgaaacctc aagaaagttg tgaagaaaat cgaagaaaaa cgatttgcaa   1020
accgaatttg aatttgaatt caaattcagt taattctgcg gttggatcga ttaagcgtgt   1080
gaagaagaaa gatgaagaaa ttgctcaggt tcaaccgaag aagctgtttg aaggtgaaaa   1140
atcagtgaag aaatcgttga acaaggtag aattgttgca agccggtata attccggtgg    1200
tggtggtggt gatgcgagga aaagatcgtt ttcggagaat aataagggtt tagggagtga   1260
aatcagggct aagaagagat gggagatacc aattgaagaa gtggatgtga gtggtttgt    1320 tatgttaccg aagatttcga caatgaggtt tgttgatgag agtcctagag attctggtgc   1380
tgttaaaaga gttgctgaat tgaatggaaa aagatcttac ttttgtgatg aagatgagga   1440
ggagagagtg atggtggagg aagaaggtgg ttctgtttgt caggttttga attttgctga   1500
agatgatgat gatgatgatg attatggtga acaagggtaa ttgtgaaat tggaattgat    1560 ttgttttttgt ggggttgtgt ggaactggct atgttctgct tgattctttt gcattttggt   1620
gtgaaactaa agatgaggtg aaaagtttat gcttgttaaa ttggattggt ttatatgttt   1680
tgaaataata acaacaagca tgtgtcttgc ttaataattg tatattgttt tgtttgtttt    1740
ataatgatat ggatttaatt tgtatacaca atataatata gtatgcattg agagagtttt   1800
tcgttcagta ttcattctga ttttagtgtt tatctcattc tagaagattg tattttgttg   1860

<210> SEQ ID NO 6
<211> LENGTH: 394
```

```
<212> TYPE: PRT
<213> ORGANISM: Medicago trunculata
<220> FEATURE:
<223> OTHER INFORMATION: Seedy1 protein

<400> SEQUENCE: 6

Met Asn Asn Thr Asn Asn Asn Asn Ile Leu Leu His Ser Thr Gln Val
1               5                   10                  15

Gln Val Trp Asn Asn Ala Ala Phe Asp Gly Glu Asp Phe Ala Met Asn
            20                  25                  30

Ser Ser Ser Asp Ser Ile Lys Glu Asn Leu Asn Pro Ser Ala Phe Asn
        35                  40                  45

Ile Val Pro Ser Ser Asn Lys Arg Thr Ile Asp Asp Glu Ile Ala Glu
    50                  55                  60

Ile Glu Ser Glu Ile Lys Arg Leu Thr Ser Lys Leu Glu Leu Leu Arg
65                  70                  75                  80

Val Glu Lys Ala Glu Arg Lys Ile Ala Ser Glu Lys Arg Val Ser Gly
                85                  90                  95

Ile Gly Thr Gly Arg Ile Val Ala Ala Lys Phe Met Glu Pro Lys Lys
            100                 105                 110

Asn Val Thr Pro Lys Arg Asn Gly Val Val Phe Lys Glu Thr Pro
        115                 120                 125

Lys Arg Asn Gly Val Val Ser Asp Thr Pro Lys Ser Arg Val Asn Trp
    130                 135                 140

Arg Arg Gly Met Ser Leu Gly Pro Met Glu Ile Ala Gly Lys Val Met
145                 150                 155                 160

Ala Pro Pro Ala Met Thr Ile Thr Pro Ala Thr Val Asn Arg Arg Lys
                165                 170                 175

Ser Cys Phe Trp Lys Pro Gln Glu Ser Cys Glu Val Met Pro Ser Gly
            180                 185                 190

Ile Thr Pro Ala Thr Val Asn Arg Arg Lys Ser Cys Phe Leu Lys Pro
        195                 200                 205

Gln Glu Ser Cys Glu Glu Asn Arg Arg Lys Thr Ile Cys Lys Pro Asn
    210                 215                 220

Leu Asn Leu Asn Ser Asn Ser Val Asn Ser Ala Val Gly Ser Ile Lys
225                 230                 235                 240

Arg Val Lys Lys Lys Asp Glu Glu Ile Ala Gln Val Gln Pro Lys Lys
                245                 250                 255

Leu Phe Glu Gly Glu Lys Ser Val Lys Lys Ser Leu Lys Gln Gly Arg
            260                 265                 270

Ile Val Ala Ser Arg Tyr Asn Ser Gly Gly Gly Gly Asp Ala Arg
        275                 280                 285

Lys Arg Ser Phe Ser Glu Asn Asn Lys Gly Leu Gly Ser Glu Ile Arg
    290                 295                 300

Ala Lys Lys Arg Trp Glu Ile Pro Ile Glu Glu Val Asp Val Ser Gly
305                 310                 315                 320

Phe Val Met Leu Pro Lys Ile Ser Thr Met Arg Phe Val Asp Glu Ser
                325                 330                 335

Pro Arg Asp Ser Gly Ala Val Lys Arg Val Ala Glu Leu Asn Gly Lys
            340                 345                 350

Arg Ser Tyr Phe Cys Asp Glu Asp Glu Glu Arg Val Met Val Glu
        355                 360                 365

Glu Glu Gly Gly Ser Val Cys Gln Val Leu Asn Phe Ala Glu Asp Asp
    370                 375                 380

Asp Asp Asp Asp Asp Tyr Gly Glu Gln Gly
```

<210> SEQ ID NO 7
<211> LENGTH: 674
<212> TYPE: DNA
<213> ORGANISM: Saccharum sp.
<220> FEATURE:
<223> OTHER INFORMATION: Seedy1 coding sequence (partial 5' end)
<220> FEATURE:
<221> NAME/KEY: modified_base
<222> LOCATION: (362)..(362)
<223> OTHER INFORMATION: a, c, t or g
<220> FEATURE:
<221> NAME/KEY: modified_base
<222> LOCATION: (372)..(372)
<223> OTHER INFORMATION: a, c, t or g
<220> FEATURE:
<221> NAME/KEY: modified_base
<222> LOCATION: (674)..(674)
<223> OTHER INFORMATION: a, c, t or g

<400> SEQUENCE: 7

```
cgcaccgcga gtttcgaaaa accaacctat cgcgcctcag atcacgcgag gacgcgaggg      60
gaagcaggaa tccctccgct cccagccgcc tcctccgctc acccatcgat cgatcgtccg     120
tccggtccag ggggctctcc ggcggcggtg gcgatggagg aggacccgct catcccgctg     180
gtgcacgtct ggaacaacgc cgccttcgac cacgcctcct cctccgcgtg gcacgcccac     240
tcccctgtgc ccgcgagcgc acgtcgcgag gcggaggggg acaaggagaa ccaccgcccc     300
gaccccgacc ccgacgtcga ggcggagatc ggccacatcg aggcggagat cctgcgcctg     360
tnctcccgcc tncaccacct tcgcacctcc aagcagtcgg agccgtccaa gcgcggagag     420
gtcgcgcccg cgcccgcggc gaaggcgaaa gcggcggcgg cggcgcggct gcggacgcgg     480
gggctcagcc tgggcccgct cgacgtcgcc gctgccggta accccaaccc gctcaccacc     540
gacaaccagc agcagcagcc gcgtgccgcg cagggtctga agccgatcaa gcaggccacg     600
gcggcggcgg gcaagggcgt aagacttggg ccccttcgac atggtcggcg cgaaccctag     660
ggtccctccg cccn                                                       674
```

<210> SEQ ID NO 8
<211> LENGTH: 166
<212> TYPE: PRT
<213> ORGANISM: Saccharum sp.
<220> FEATURE:
<223> OTHER INFORMATION: Seedy1 protein (partial N term)
<220> FEATURE:
<221> NAME/KEY: MOD_RES
<222> LOCATION: (70)..(70)
<223> OTHER INFORMATION: Any amino acid

<400> SEQUENCE: 8

```
Met Glu Glu Asp Pro Leu Ile Pro Leu Val His Val Trp Asn Asn Ala
1               5                   10                  15

Ala Phe Asp His Ala Ser Ser Ser Ala Trp His Ala His Ser Pro Val
            20                  25                  30

Pro Ala Ser Ala Arg Arg Glu Ala Glu Gly Asp Lys Glu Asn His Arg
        35                  40                  45

Pro Asp Pro Asp Pro Asp Val Glu Ala Glu Ile Gly His Ile Glu Ala
    50                  55                  60

Glu Ile Leu Arg Leu Xaa Ser Arg Leu His His Leu Arg Thr Ser Lys
65                  70                  75                  80

Gln Ser Glu Pro Ser Lys Arg Gly Glu Val Ala Pro Ala Pro Ala Ala
                85                  90                  95
```

Lys Ala Lys Ala Ala Ala Ala Ala Arg Leu Arg Thr Arg Gly Leu Ser
            100                 105                 110

Leu Gly Pro Leu Asp Val Ala Ala Ala Gly Asn Pro Asn Pro Leu Thr
        115                 120                 125

Thr Asp Asn Gln Gln Gln Gln Pro Arg Ala Ala Gln Gly Leu Lys Pro
    130                 135                 140

Ile Lys Gln Ala Thr Ala Ala Ala Gly Lys Gly Val Arg Leu Gly Pro
145                 150                 155                 160

Leu Arg His Gly Arg Arg
                165

<210> SEQ ID NO 9
<211> LENGTH: 876
<212> TYPE: DNA
<213> ORGANISM: Zea mays
<220> FEATURE:
<223> OTHER INFORMATION: Seedy1 coding sequence (partial 3' end)
<220> FEATURE:
<221> NAME/KEY: modified_base
<222> LOCATION: (869)..(869)
<223> OTHER INFORMATION: a, c, t or g

<400> SEQUENCE: 9
ccacgcgtcc ggccgttcga gaggaggaag gccagcgttc aaggagcac gccgtccccg      60
ccagaccgtg gccatccagc aatgccaggc acccactgga tgccaggcaa ggcaccgcag    120
caagcagagc caaggcgagg agcgggagca taagccccag caggttcagg aggcagtcca    180
cttccaaggc tgccgagaca agagcggaa atgccaagcc tacagaggcg acgaggggag     240
ggagcgaagc ggtcaatcac accagcaatg tagccacgac gaagaggccg gcggggagct    300
ccaaggtcag ggttgtcccg agccgctaca gcatcccacc tggctcctcc ctagcagctg    360
tgacacaagg caaccgatgc aagcagtctc tcccaggatc ggctactgag accagagtaa    420
atctcactga gccgccgaac gacgagttgt ctcctgaaga acttgccaag gttgcagagc    480
tgctcccaag gattaggacc atgccgcctt ctgatgagag cccgcgtgac tcgggatgtg    540
ccaagcgtgt tgctgatttg gtcgggaagc gatccttctt cactgctgca ggggacgatg    600
gcaatctcgt tacgccctac caggcacggg tggttgaact tgaatcaccc gaggcagcag    660
cagaagaagc agaagcttga gaagtttgtc tttgatcaat tccgaagtgg cttgcatctg    720
ggcgtggcct ctttttgcag tgtgtgctac tacatagtct actgttacat tcatatcata    780
tcacatttcc tatttttttcc cccttgagac attgcttagt acttttgtgt tgccttgtga    840
aaagagagtg gaaggttcat ctgctgatnc cttgtt                              876

<210> SEQ ID NO 10
<211> LENGTH: 224
<212> TYPE: PRT
<213> ORGANISM: Zea mays
<220> FEATURE:
<223> OTHER INFORMATION: Seedy1 protein (partial C term)

<400> SEQUENCE: 10

Thr Arg Pro Ala Val Arg Glu Glu Glu Gly Gln Arg Ser Lys Glu His
1               5                   10                  15

Ala Val Pro Ala Arg Pro Trp Pro Ser Ser Asn Ala Arg His Pro Leu
            20                  25                  30

Asp Ala Arg Gln Gly Thr Ala Ala Ser Arg Ala Lys Ala Arg Ser Gly
        35                  40                  45

Ser Ile Ser Pro Ser Arg Phe Arg Gln Ser Thr Ser Lys Ala Ala
    50                  55                  60

| | | | | | | | | | | | | | | |
|---|---|---|---|---|---|---|---|---|---|---|---|---|---|---|
|Glu|Thr|Arg|Ala|Gly|Asn|Ala|Lys|Pro|Thr|Glu|Ala|Thr|Arg|Gly|Gly|
|65| | | | |70| | | | |75| | | | |80|

Ser Glu Ala Val Asn His Thr Ser Asn Val Ala Thr Thr Lys Arg Pro
                85                  90                  95

Ala Gly Ser Ser Lys Val Arg Val Pro Ser Arg Tyr Ser Ile Pro
            100                 105                 110

Pro Gly Ser Ser Leu Ala Ala Val Thr Gln Gly Asn Arg Cys Lys Gln
            115                 120                 125

Ser Leu Pro Gly Ser Ala Thr Glu Thr Arg Val Asn Leu Thr Glu Pro
            130                 135                 140

Pro Asn Asp Glu Leu Ser Pro Glu Glu Leu Ala Lys Val Ala Glu Leu
145                 150                 155                 160

Leu Pro Arg Ile Arg Thr Met Pro Pro Ser Asp Glu Ser Pro Arg Asp
                165                 170                 175

Ser Gly Cys Ala Lys Arg Val Ala Asp Leu Val Gly Lys Arg Ser Phe
            180                 185                 190

Phe Thr Ala Ala Gly Asp Asp Gly Asn Leu Val Thr Pro Tyr Gln Ala
            195                 200                 205

Arg Val Val Glu Leu Glu Ser Pro Glu Ala Ala Glu Glu Ala Glu
            210                 215                 220

```
<210> SEQ ID NO 11
<211> LENGTH: 1257
<212> TYPE: DNA
<213> ORGANISM: Arabidopsis thaliana
<220> FEATURE:
<223> OTHER INFORMATION: Seedy1 coding sequence

<400> SEQUENCE: 11
atgacatcaa ttgaggcaac agaaacgctt aacgctcctc caaagcttca gatctggaac    60
aacgctgcct cgacgatgg agattctcaa atcacttccg ccatcgaagc ttcttcttgg   120
tctcacctca acgaatcatt cgattccgat gtagcaagg agaatcagtt ccgatttcg    180 gtttcctctt cgctccaatc ctcagtctcg atcaccgaag ctccgtcagc aaaatccaag   240
accgtgaaga ccaaatccgc cgcagatcgg agtaaaaagc gagatatcga tgcagagatc   300
gaagaagtag agaaggagat cggacgatta tcgacgaaat ggagtcgct ccgattagag   360 aaggcggagc aaaccgcaag aagcattgct atacgtggaa gaatcgttcc ggcgaagttc   420
atggaatcat ctcagaaaca agtgaaattc gacgattcgt gttttacagg atcgaaatca   480
agagccactc gtagaggcgt tagtcttgga ccagcggaga tattcaattc cgcgaagaaa   540
tctgaaactg tgactcctct tcaatcagct cagaatcgac gcaagtcttg tttcttaag   600 cttcctggaa tcgaagaagg tcaagtgacg acacgaggta aaggaagaac gagtttgagt   660
ctgagtccga gatctcgcaa agcgaaaatg acggcagctc agaagcaagc agctacgacg   720 gtgggtcaa agagagctgt gaagaaagaa gaaggagttc tcttaacaat ccagcctaag   780
aggctattca agaagatgaa aagaatgtt tctttaagga aaccattgaa accaggaaga   840
gttgtggcta gtaggtacag tcaaatgggt aaaacgcaga ctggagagaa agatgttagg   900
aaaaggtcgt tgcctgagga tgaagagaaa gagaatcata gaggtcgga gaagagaaga    960 gcttctgatg aaagtaacaa gagtgaaggg agagtgaaga agagatggga gattccaagt  1020
gaagttgatc tgtatagcag tggtgagaac ggtgacgagt ctcctatagt taaggagcta  1080
cctaagatca gaacgcttcg tcgtgtggga gggagcctc gtgattcagg tgctgctaag  1140
agagttgcag aattacaagc caaggatcgt aacttcactt tttgccagct tctgaagttt  1200
```
gaagaatgaa tgatccgctt atcaatttga gtaaaatcca caactcttgt tgtggtt        1257

<210> SEQ ID NO 12
<211> LENGTH: 402
<212> TYPE: PRT
<213> ORGANISM: Arabidopsis thaliana
<220> FEATURE:
<223> OTHER INFORMATION: Seedy1 protein

<400> SEQUENCE: 12

```
Met Thr Ser Ile Glu Ala Thr Glu Thr Leu Asn Ala Pro Pro Lys Leu
1               5                   10                  15

Gln Ile Trp Asn Asn Ala Ala Phe Asp Asp Gly Asp Ser Gln Ile Thr
            20                  25                  30

Ser Ala Ile Glu Ala Ser Ser Trp Ser His Leu Asn Glu Ser Phe Asp
        35                  40                  45

Ser Asp Cys Ser Lys Glu Asn Gln Phe Pro Ile Ser Val Ser Ser Ser
    50                  55                  60

Leu Gln Ser Ser Val Ser Ile Thr Glu Ala Pro Ser Ala Lys Ser Lys
65                  70                  75                  80

Thr Val Lys Thr Lys Ser Ala Ala Asp Arg Ser Lys Lys Arg Asp Ile
                85                  90                  95

Asp Ala Glu Ile Glu Glu Val Glu Lys Glu Ile Gly Arg Leu Ser Thr
            100                 105                 110

Lys Leu Glu Ser Leu Arg Leu Glu Lys Ala Glu Gln Thr Ala Arg Ser
        115                 120                 125

Ile Ala Ile Arg Gly Arg Ile Val Pro Ala Lys Phe Met Glu Ser Ser
    130                 135                 140

Gln Lys Gln Val Lys Phe Asp Asp Ser Cys Phe Thr Gly Ser Lys Ser
145                 150                 155                 160

Arg Ala Thr Arg Arg Gly Val Ser Leu Gly Pro Ala Glu Ile Phe Asn
                165                 170                 175

Ser Ala Lys Lys Ser Glu Thr Val Thr Pro Leu Gln Ser Ala Gln Asn
            180                 185                 190

Arg Arg Lys Ser Cys Phe Phe Lys Leu Pro Gly Ile Glu Glu Gly Gln
        195                 200                 205

Val Thr Thr Arg Gly Lys Gly Arg Thr Ser Leu Ser Leu Ser Pro Arg
    210                 215                 220

Ser Arg Lys Ala Lys Met Thr Ala Ala Gln Lys Gln Ala Ala Thr Thr
225                 230                 235                 240

Val Gly Ser Lys Arg Ala Val Lys Lys Glu Glu Gly Val Leu Leu Thr
                245                 250                 255

Ile Gln Pro Lys Arg Leu Phe Lys Glu Asp Glu Lys Asn Val Ser Leu
            260                 265                 270

Arg Lys Pro Leu Lys Pro Gly Arg Val Val Ala Ser Arg Tyr Ser Gln
        275                 280                 285

Met Gly Lys Thr Gln Thr Gly Glu Lys Asp Val Arg Lys Arg Ser Leu
    290                 295                 300

Pro Glu Asp Glu Glu Lys Glu Asn His Lys Arg Ser Glu Lys Arg Arg
305                 310                 315                 320

Ala Ser Asp Glu Ser Asn Lys Ser Glu Gly Arg Val Lys Lys Arg Trp
                325                 330                 335

Glu Ile Pro Ser Glu Val Asp Leu Tyr Ser Ser Gly Glu Asn Gly Asp
            340                 345                 350

Glu Ser Pro Ile Val Lys Glu Leu Pro Lys Ile Arg Thr Leu Arg Arg
```

```
            355                 360                 365
Val Gly Gly Ser Pro Arg Asp Ser Gly Ala Ala Lys Arg Val Ala Glu
        370                 375                 380

Leu Gln Ala Lys Asp Arg Asn Phe Thr Phe Cys Gln Leu Leu Lys Phe
385                 390                 395                 400

Glu Glu

<210> SEQ ID NO 13
<211> LENGTH: 3074
<212> TYPE: DNA
<213> ORGANISM: Artificial Sequence
<220> FEATURE:
<223> OTHER INFORMATION: Description of Artificial Sequence: Synthetic
      [PRO0090-CDS0689-terminator] expression cassette
      polynucleotide

<400> SEQUENCE: 13
cttctacatc ggcttaggtg tagcaacacg actttattat tattattatt attattatta      60
ttattttaca aaatatataaa atagatcagt ccctcaccac aagtagagca agttggtgag    120
ttattgtaaa gttctacaaa gctaatttaa aagttattgc attaacttat ttcatattac    180
aaacaagagt gtcaatggaa caatgaaaac catatgacat actataattt tgttttattt    240
attgaaatta taattcaa agagaataaa tccacatagc cgtaaagttc tacatgtggt      300
gcattaccaa aatatatata gcttacaaaa catgacaagc ttagtttgaa aaattgcaat    360
ccttatcaca ttgacacata aagtgagtga tgagtcataa tattattttc tttgctaccc    420
atcatgtata tatgatagcc acaaagttac tttgatgatg atatcaaaga acattttag     480 gtgcacctaa cagaatatcc aaataatatg actcacttag atcataatag agcatcaagt    540
aaaactaaca ctctaaagca accgatggga aagcatctat aaatagacaa gcacaatgaa    600
aatcctcatc atccttcacc acaattcaaa tattatagtt gaagcatagt agtaatttaa    660
atcaactagg gatatcacaa gtttgtacaa aaaagcaggc tggtaccggt ccggaattcc    720
cgggatatcg tcgacccacg cgtccgctga cgcgtgggtt ccactacatc aagacatcta    780
ctacactcat ctttttttgca cttattgggt gtaaattttt gaaacccagt tgagaaaaat    840
gagtgtgtta caatacccag aagggattga cccagcagat gttcagatat ggaacaatgc    900
agcatttgat aatggagatt ctgaagattt gtcttcgctg aaacgttctt ggtctcctct    960
gaaacccctt tcggttaggc catcagattc ctttgaatct gatttgtcaa gtaaggaaaa   1020
tcaaactcct ttattgaga attcatctgt taatctctca tctccgttac ccataaagcc    1080
acttaaccct aatggggctc tggaaaattc aagactcaag ccgaacaagc ccaattccaa   1140
acagagtctt gatgagatgg cggctagaaa gagcggaaag ggaaatgatt tccgtgatga   1200
gaagaaaata gacgaggaaa ttgaagaaat tcagatggag attagtaggt tgagttcaag    1260
attagaggct ttgagaattg aaaaggctga gaaaactgtt gctaagactg ttgaaaagcg    1320
aggaagggtt gtggcagcaa agtttatgga gccaaaacaa agtgttatta agattgaaga    1380
gcgtatatca atgagtgcaa gaacaaaggt ggagcagaga aggggtctta gtttaggacc    1440
atctgagatt tttactggaa cgcggcggcg agggttgagt atgggccat cagatattct    1500 agcagggaca acaaaggcac ggcaattggg aaagcaagag atgattatta ctcctattca   1560
gccaatacaa aacaggcgaa agtcgtgttt ttggaagctt caagagattg aagaagaggg    1620
aaaaagttca agcctagtc ctaaatcaag aaaaactgct gcaagaacaa tggttacaac    1680
aaggcaggca gttactacaa ttgcatcaaa gaagaatttg aaaaagatg atggacttt     1740
```

-continued

```
gagttcagtt cagccaaaga agttgtttaa agatctcgaa aagtctgctg ctgctaataa    1800
gaagccccag aggccgggga gggttgtggc tagtaggtat aatcagagta caattcagtc    1860
atcagtagtg agaaagaggt ctttacctga aaatgataag gatgagagta agagaaatga    1920
taagaaacgg tcgttatctg tagggaaaac gcgtgtgtct caaactgaga gcaagaattt    1980
gggtactgaa agtagggtga aaagagatg ggaaattcct agtgagattg tagttcatgg      2040
aaacacagag agtgagaaat ctccactaag cattattgtg aagcctgatt tgcttccgcg    2100
aattaggatt gctcggtgtg tgaatgagac tcttagggat tctggacctg ctaaaagaat    2160
gatagagttg ataggcaaga aatcgttttt cagtagtgat gaagataagg agccacctgt    2220
ctgtcaagtt ttaagttttg cagaggaaga tgctgaagag gaataatgtg taataaaggg    2280
agctgctaac tcttttcatg ctctttcaat tttcaatcct gccttttaat ttttgttcat    2340
tcgtgccttt taattgaatg gggaagcatt cttttgcttc ctcaaactgg tattctagct    2400
tctgaattac attgtatggt acaatatgaa taaggttttg tcttccggca ggttgtccaa    2460
gttagttttt agcttaaaat agatgcggca gcggccgctc tagagtatcc ctcgaggggc    2520
ccaagcttac gcgtacccag ctttcttgta caaagtggtg atatcacaag cccgggcggt    2580
cttctaggga taacagggta attatatccc tctagatcac aagcccgggc ggtcttctac    2640
gatgattgag taataatgtg tcacgcatca ccatgggtgg cagtgtcagt gtgagcaatg    2700
acctgaatga acaattgaaa tgaaagaaa aaaagtactc catctgttcc aaattaaaat      2760 tcatttttaac cttttaatag gtttatacaa taattgatat atgttttctg tatatgtcta    2820
atttgttatc atccgggcgg tcttctaggg ataacagggt aattatatcc ctctagacaa    2880
cacacaacaa ataagagaaa aaacaaataa tattaatttg agaatgaaca aaaggaccat    2940
atcattcatt aactcttctc catccatttc catttcacag ttcgatagcg aaaaccgaat    3000
aaaaaacaca gtaaattaca agcacaacaa atggtacaag aaaaacagtt ttcccaatgc    3060
cataatactc gaac                                                       3074
```

<210> SEQ ID NO 14
<211> LENGTH: 668
<212> TYPE: DNA
<213> ORGANISM: Oryza sativa
<220> FEATURE:
<223> OTHER INFORMATION: Prolamin RP6 promoter sequence

<400> SEQUENCE: 14

```
ccttctacat cggcttaggt gtagcaacac gactttatta ttattattat tattattatt      60
attattttac aaaaatataa aatagatcag tccctcacca caagtagagc aagttggtga     120
gttattgtaa agttctacaa agctaattta aagttattg cattaactta tttcatatta     180
caaacaagag tgtcaatgga acaatgaaaa ccatatgaca tactataatt ttgtttttat    240
tattgaaatt atataattca aagagaataa atccacatag ccgtaaagtt ctacatgtgg    300
tgcattacca aaatatatat agcttacaaa acatgacaag cttagtttga aaaattgcaa    360
tccttatcac attgacacat aaagtgagtg atgagtcata atattatttt tcttgctacc    420
catcatgtat atatgatagc cacaaagtta ctttgatgat gatatcaaag aacatttta     480 ggtgcaccta acagaatatc caaataatat gactcactta gatcataata gagcatcaag    540
taaaactaac actctaaagc aaccgatggg aaagcatcta taaatagaca agcacaatga    600
aaatcctcat catccttcac cacaattcaa atattatagt tgaagcatag tagtagaatc    660
caacaaca                                                              668
```

```
<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (3)..(3)
<223> OTHER INFORMATION: Val, Leu or His
<220> FEATURE:
<221> NAME/KEY: MOD_RES
<222> LOCATION: (4)..(4)
<223> OTHER INFORMATION: Gln or His
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(10)
<223> OTHER INFORMATION: Ala or Pro
<220> FEATURE:
<221> NAME/KEY: MOD_RES
<222> LOCATION: (11)..(11)
<223> OTHER INFORMATION: Phe or Cys
<220> FEATURE:
<223> OTHER INFORMATION: See specification as filed for detailed
      description of substitutions and preferred embodiments

<400> SEQUENCE: 15

Xaa Xaa Xaa Xaa Xaa Trp Xaa Asn Ala Xaa Xaa Asp
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      Motif 2 CORE peptide
<220> FEATURE:
<221> NAME/KEY: MOD_RES
<222> LOCATION: (4)..(5)
<223> OTHER INFORMATION: Any amino acid

<400> SEQUENCE: 16

Lys Glu Asn Xaa Xaa Pro
1               5

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, Val or Ala
<220> FEATURE:
<221> NAME/KEY: MOD_RES
<222> LOCATION: (2)..(2)
<223> OTHER INFORMATION: Asp or Glu
<220> FEATURE:
```

```
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Ile or Met
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (8)..(8)
<223> OTHER INFORMATION: Ile or Val
<220> FEATURE:
<221> NAME/KEY: MOD_RES
<222> LOCATION: (9)..(9)
<223> OTHER INFORMATION: Glu or Gln
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (17)..(17)
<223> OTHER INFORMATION: Ser, Thr, Leu, Ile or Ala
<220> FEATURE:
<221> NAME/KEY: MOD_RES
<222> LOCATION: (18)..(18)
<223> OTHER INFORMATION: Arg or Lys
<220> FEATURE:
<221> NAME/KEY: MOD_RES
<222> LOCATION: (20)..(21)
<223> OTHER INFORMATION: Any amino acid
<220> FEATURE:
<221> NAME/KEY: MOD_RES
<222> LOCATION: (24)..(24)
<223> OTHER INFORMATION: Leu, Val, Thr or Ile
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (26)..(26)
<223> OTHER INFORMATION: Lys or Gln
<220> FEATURE:
<223> OTHER INFORMATION: See specification as filed for detailed
      description of substitutions and preferred embodiments

<400> SEQUENCE: 17

Xaa Xaa Xaa Glu Xaa Xaa Xaa Xaa Xaa Xaa Glu Xaa Xaa Arg Leu Xaa
1               5                   10                  15

Xaa Xaa Leu Xaa Xaa Leu Arg Xaa Xaa Xaa
            20                  25

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Lys
<220> FEATURE:
```

```
<221> NAME/KEY: MOD_RES
<222> LOCATION: (5)..(5)
<223> OTHER INFORMATION: Arg, Ser or Lys
<220> FEATURE:
<221> NAME/KEY: MOD_RES
<222> LOCATION: (6)..(6)
<223> OTHER INFORMATION: Thr or Ile
<220> FEATURE:
<221> NAME/KEY: MOD_RES
<222> LOCATION: (7)..(7)
<223> OTHER INFORMATION: Met, Leu, Ala or Val
<220> FEATURE:
<221> NAME/KEY: MOD_RES
<222> LOCATION: (8)..(8)
<223> OTHER INFORMATION: Pro or Arg
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (11)..(11)
<223> OTHER INFORMATION: Asp, Gln, Thr or Asn
<220> FEATURE:
<221> NAME/KEY: MOD_RES
<222> LOCATION: (12)..(12)
<223> OTHER INFORMATION: Glu or Gly
<220> FEATURE:
<221> NAME/KEY: MOD_RES
<222> LOCATION: (13)..(13)
<223> OTHER INFORMATION: Ser or Thr
<220> FEATURE:
<221> NAME/KEY: MOD_RES
<222> LOCATION: (14)..(14)
<223> OTHER INFORMATION: Pro or Leu
<220> FEATURE:
<221> NAME/KEY: MOD_RES
<222> LOCATION: (19)..(19)
<223> OTHER INFORMATION: Cys, Pro or Ala
<220> FEATURE:
<221> NAME/KEY: MOD_RES
<222> LOCATION: (20)..(20)
<223> OTHER INFORMATION: Ala, Val or Ile
<220> FEATURE:
<221> NAME/KEY: MOD_RES
<222> LOCATION: (23)..(23)
<223> OTHER INFORMATION: Val, Gln, Asn or Ile
<220> FEATURE:
<221> NAME/KEY: MOD_RES
<222> LOCATION: (24)..(24)
<223> OTHER INFORMATION: Ala or Ile
<220> FEATURE:
<221> NAME/KEY: MOD_RES
<222> LOCATION: (25)..(25)
<223> OTHER INFORMATION: Asp or Glu
<220> FEATURE:
<221> NAME/KEY: MOD_RES
<222> LOCATION: (26)..(26)
<223> OTHER INFORMATION: Leu or Arg
<220> FEATURE:
<221> NAME/KEY: MOD_RES
<222> LOCATION: (27)..(27)
<223> OTHER INFORMATION: Val, Gln, Asn or Ile
<220> FEATURE:
<221> NAME/KEY: MOD_RES
<222> LOCATION: (28)..(28)
<223> OTHER INFORMATION: Gly or Ala
<220> FEATURE:
<223> OTHER INFORMATION: See specification as filed for detailed
      description of substitutions and preferred embodiments

<400> SEQUENCE: 18

Leu Pro Xaa Ile Xaa Xaa Xaa Xaa Xaa Xaa Xaa Xaa Xaa Xaa Arg Asp
1               5                   10                  15

Ser Gly Xaa Xaa Lys Arg Xaa Xaa Xaa Xaa Xaa Xaa Lys
            20                  25
```

-continued

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tttttttttt tttttttttt ttttt                                         25

<210> SEQ ID NO 21
<211> LENGTH: 81
<212> TYPE: PRT
<213> ORGANISM: Arabidopsis thaliana

<400> SEQUENCE: 21

Met Met Glu Glu Asp Pro Leu Ile Pro Leu Val His Val Trp Thr Asn
1               5                   10                  15

Ala Ala Phe Asp Ser Ser Ser Ser Ser Ala Trp His Ala His Ala
            20                  25                  30

Thr Pro Val Arg Arg Gly Glu Lys Glu Asn Arg Arg Pro Ala Glu Thr
        35                  40                  45

Asn Asp Ala Asp Ala Glu Ile Ala Arg Ile Glu Ala Glu Ile Leu Arg
    50                  55                  60

Leu Ser Ser Arg Leu His His Leu Arg Val Ser Lys Gly His Asp Ala
65                  70                  75                  80

Lys

<210> SEQ ID NO 22
<211> LENGTH: 84
<212> TYPE: PRT
<213> ORGANISM: Zea mays

<400> SEQUENCE: 22

Met Glu Glu Asp Pro Leu Ile Gln Leu Val His Val Trp Ser Asn Ala
1               5                   10                  15

Ala Cys Asp Asn Ala Ala Ala Ser Ser Ser Val Cys His Ala His Ser
            20                  25                  30

Pro Ala Pro Ala Ser Ala Arg Glu Gly Glu Gly Asp Lys Glu Asn Leu
        35                  40                  45

Arg Arg Glu Pro Asp Val Glu Glu Met Arg His Ile Glu Ala Glu
    50                  55                  60

Ile Leu Arg Leu Ser Leu Arg Leu His His Leu Arg Thr Ser Gln Gln
65                  70                  75                  80

Leu Gln Pro Pro

<210> SEQ ID NO 23
<211> LENGTH: 85
<212> TYPE: PRT
```

<213> ORGANISM: Saccharum sp.

<400> SEQUENCE: 23

Met Glu Glu Asp Pro Leu Ile Pro Leu Val His Val Trp Asn Asn Ala
1               5                   10                  15

Pro Phe Asp His Ala Ser Tyr Ser Ala Trp His Ala His Ser Pro Ala
                20                  25                  30

Arg Ala Ser Ala Gly His Glu Ala Glu Gly Asp Lys Glu Asn His Arg
            35                  40                  45

Pro Asp Pro Asp Pro Asp Val Glu Ala Glu Ile Gly His Ile Glu Ala
        50                  55                  60

Glu Ile Leu Arg Leu Ser Ser Arg Leu His His Leu Arg Thr Ser Lys
65                  70                  75                  80

Gln Ser Glu Pro Pro
                85

<210> SEQ ID NO 24
<211> LENGTH: 125
<212> TYPE: PRT
<213> ORGANISM: Brassica napus

<400> SEQUENCE: 24

Met Thr Ser Thr Glu His Thr Glu Thr Leu Asn Ala Pro Glu Leu Gln
1               5                   10                  15

Ile Trp Asn Asn Ala Ala Phe Asp Asp Gly Asp Ser Asn Leu Thr Ser
                20                  25                  30

Ala Ile Glu Ala Ser Trp Ser Asn Leu Asn Ala Ser Phe Asp Ser Asp
            35                  40                  45

Cys Ser Lys Glu Asn Gln Ile Pro Val Ser Val Ser Ser Ser Leu Lys
        50                  55                  60

Ser Ser Val Ser Phe Ser Thr Asp Asp Pro Ile Arg Cys Gly Lys Val
65                  70                  75                  80

Lys Glu Lys Pro His Lys Thr Gly Lys Val Arg His Gly Asp Ile Asp
                85                  90                  95

Ala Glu Ile Glu Glu Val Glu Lys Glu Met Asn Arg Leu Ser Ile Arg
            100                 105                 110

Leu Glu Ser Leu Arg Leu Glu Lys Ala Glu Gln Ile Ala
        115                 120                 125

<210> SEQ ID NO 25
<211> LENGTH: 86
<212> TYPE: PRT
<213> ORGANISM: Eschscholzia californica

<400> SEQUENCE: 25

Met Leu Glu Ile Ser Glu Thr Leu Asn Leu Pro Asp Leu Gln Thr Trp
1               5                   10                  15

Asn Asn Ala Ala Phe Asp Ser Gly Ser Thr Asp Asn His Thr Thr Ala
                20                  25                  30

Ile Lys Ala Ser Ser Ser Pro Leu Lys Pro Ile Val Leu Asn Gln Ser
            35                  40                  45

Glu Pro Ser Ile Leu Asp Ser Ile Tyr Thr Lys Glu Asn Gln Thr Pro
        50                  55                  60

Ser Cys Cys Ile Ser Pro Val Arg Thr Lys Ser Pro Leu Pro Ile Lys
65                  70                  75                  80

Pro Leu His Pro Asn Gly
                85

```
<210> SEQ ID NO 26
<211> LENGTH: 144
<212> TYPE: PRT
<213> ORGANISM: Gossypium arboreum

<400> SEQUENCE: 26

Met Ser Ile Leu Gln Tyr Pro Asp Ser Phe Asn Val Pro Glu Leu Gln
1               5                   10                  15

Val Trp Asn Asn Ala Ala Phe Asp Asn Gly Asp Ser Glu Asp Thr Asn
            20                  25                  30

Ala Ile Lys Asp Ser Trp Cys Asn Phe Asn Ser Gly Ser Val Asn Gln
        35                  40                  45

Ser Leu Glu Ser Asp Gly Ser Lys Glu Asn Gln Ser Pro Leu Trp Ile
    50                  55                  60

Lys Ser Pro Val Ser Phe Lys Ser Thr Ala Ser Val Val Lys Pro Leu
65                  70                  75                  80

Ser Ser Lys Asn Val Thr Gly Asn Thr Arg Glu Pro Phe Ser Ala Lys
                85                  90                  95

Met Lys Ser Gly Val Cys Lys Glu Glu Glu Lys Lys Arg Asp Glu Lys
            100                 105                 110

Lys Ile Asp Met Glu Ile Glu Glu Ile Glu Lys Glu Val Ala Arg Leu
        115                 120                 125

Ser Ala Lys Leu Glu Ser Leu Arg Leu Glu Lys Pro Asn Ile Met Gln
    130                 135                 140

<210> SEQ ID NO 27
<211> LENGTH: 75
<212> TYPE: PRT
<213> ORGANISM: Populus tremula

<400> SEQUENCE: 27

Met Ser Ser Ile Leu Gln Tyr Pro Asp Val Asp Ala Pro Glu Val
1               5                   10                  15

Gln Ile Trp Asn Asn Ala Ala Phe Asp Asn Gly Glu Ser Glu Gly Ser
            20                  25                  30

Leu Asn Leu Lys Ser Ser Trp Trp Asn Gln Ser Leu Glu Ser Asp Ala
        35                  40                  45

Ser Lys Glu Asn Leu Ser Pro Val Cys Glu Gln Ser Ser Pro Val Phe
    50                  55                  60

Val Asn Ser Ser Lys Pro Ala Lys Pro Leu Gln
65                  70                  75

<210> SEQ ID NO 28
<211> LENGTH: 77
<212> TYPE: PRT
<213> ORGANISM: Plumbao zeylanica

<400> SEQUENCE: 28

Met Asn Glu Val Leu His Leu Gln Glu Ala Ala Arg Thr Asp Ser Ser
1               5                   10                  15

Thr Asp His Gln Ile Trp Asn Asn Ala Ala Phe Asp Ser Gly Glu Ser
            20                  25                  30

Glu Asp Ser Pro Val Val Ile Asp Phe Ser Ala Pro Asn Leu Ser Gln
        35                  40                  45

Ser Leu Leu Ser Asp Ser Ser Ile Lys Glu Asn Leu Ser Pro Ser Leu
    50                  55                  60

Ala Glu Met Pro His Pro Ala Lys Ser Pro Met Gln Lys
65                  70                  75
```

<210> SEQ ID NO 29
<211> LENGTH: 139
<212> TYPE: PRT
<213> ORGANISM: Citrus sinensis

<400> SEQUENCE: 29

Met Ser Val Leu Gln Tyr Pro Asp Thr Leu Asn Gly Gln Glu Leu Gln
1               5                   10                  15

Ile Trp Asn Asn Ala Ala Phe Asp Asn Gly Glu Ser Glu Asp Ser Thr
            20                  25                  30

Ala Met Lys Gly Ser Trp Ala Asn Leu Lys Ser Val Tyr Met Asn Gln
        35                  40                  45

Ser Leu Glu Ser Asp Cys Ser Lys Glu Asn Leu Ser Pro Arg Leu Asn
50                  55                  60

Lys Ser Pro Thr Ser Ser Leu Lys Ser Cys Val Pro Asn Lys Pro Leu
65                  70                  75                  80

Gln Val Asn Ser Ser Val Lys Asn Ser Gln Met Lys Gln Leu Lys Ser
                85                  90                  95

Val Ser Lys Glu Glu Glu Thr Arg Asp Glu Arg Lys Ile Asp Ile Glu
            100                 105                 110

Ile Glu Glu Ile Glu Lys Glu Ile Ser Arg Leu Ser Ser Arg Leu Glu
        115                 120                 125

Ala Leu Arg Leu Glu Lys Ile Asp Ile Lys Thr
    130                 135

<210> SEQ ID NO 30
<211> LENGTH: 186
<212> TYPE: PRT
<213> ORGANISM: Hordeum vulgare

<400> SEQUENCE: 30

Ile Ser Thr Ala Ser Thr Cys Arg Arg Pro Ala Gly Ser Ser Lys Val
1               5                   10                  15

Arg Val Val Pro Ser Arg Tyr Ser Leu Met Pro Gly Ala Ser Leu Gly
            20                  25                  30

Ala Ala Thr Gln Asp Gly Arg Arg Lys Glu Ser Leu Pro Gly Ser Thr
        35                  40                  45

Gly Ser Thr Gly Gln Lys Glu Glu Ile Lys Ala Val Pro Thr Glu Pro
50                  55                  60

Val Asp Asp Leu Ser Pro Glu Ser Leu Asp Lys Val Ala Glu Leu
65                  70                  75                  80

Leu Pro Arg Ile Arg Thr Met Pro Arg Pro Asn Glu Thr Pro Pro Asp
                85                  90                  95

Ser Gly Cys Ala Lys Arg Ala Ala Asp Leu Val Gly Lys Arg Ser Phe
            100                 105                 110

Phe Ala Ala Ala Ala Gly Asp Gly Ser Ala Ile Ser Ser Tyr Gln
        115                 120                 125

Ala Arg Val Leu Glu Ala Glu Ala Pro Glu Glu Ala Ala Ala Gly
    130                 135                 140

Ala Leu Ser Asp Glu Ala Ala Ala Gly Ala Leu Ser Asp Glu Ala
145                 150                 155                 160

Ala Ala Ala Ala Ala Ala Glu Ala Leu Ser Asp Glu Ala Ala Ala
                165                 170                 175

Ala Glu Ala Leu Ser Asp Glu Ala Ala Ala
            180                 185

<210> SEQ ID NO 31
<211> LENGTH: 145
<212> TYPE: PRT
<213> ORGANISM: Triticum aestivum

<400> SEQUENCE: 31

Gly Arg Tyr Ser Leu Met Pro Gly Ala Ser Leu Gly Ala Ala Ser Gln
1               5                   10                  15

Glu Arg Arg Lys Glu Ser Leu Pro Gly Ser Thr Gly Gly Ala Gly
            20                  25                  30

Gln Lys Glu Glu Glu Ile Lys Ala Met Pro Thr Glu Pro Val Asp Asp
        35                  40                  45

Asp Leu Ser Pro Glu Ser Leu Asp Lys Val Ala Glu Leu Leu Pro Arg
    50                  55                  60

Thr Arg Thr Met Pro Pro Asp Glu Thr Pro Arg Asp Ser Gly Cys
65                  70                  75                  80

Ala Lys Arg Ala Ala Asp Leu Val Gly Lys Arg Ser Phe Phe Ala Ala
                85                  90                  95

Ala Ala Ala Gly Asp Cys Ser Ala Ile Ser Ser Tyr Gln Ala Arg Val
            100                 105                 110

Leu Glu Ala Glu Ala Pro Glu Glu Ala Ala Ala Ala Glu Ala Leu
        115                 120                 125

Gly Asp Glu Ala Ala Ser Ala Gly Glu Ala Leu Gly Asp Glu Ala Ala
    130                 135                 140

Ala
145

<210> SEQ ID NO 32
<211> LENGTH: 139
<212> TYPE: PRT
<213> ORGANISM: Zea mays

<400> SEQUENCE: 32

Thr Ser Asn Val Ala Thr Thr Lys Arg Pro Ala Gly Ser Ser Lys Val
1               5                   10                  15

Arg Val Val Pro Ser Arg Tyr Ser Ile Pro Pro Gly Ser Ser Leu Ala
            20                  25                  30

Ala Val Thr Gln Gly Asn Arg Cys Lys Gln Ser Leu Pro Gly Ser Ala
        35                  40                  45

Thr Glu Thr Arg Val Asn Leu Thr Glu Pro Pro Asn Asp Glu Leu Ser
    50                  55                  60

Pro Glu Glu Leu Ala Lys Val Ala Glu Leu Leu Pro Arg Ile Arg Thr
65                  70                  75                  80

Met Pro Pro Ser Asp Glu Ser Pro Arg Asp Ser Gly Cys Ala Lys Arg
                85                  90                  95

Val Ala Asp Leu Val Gly Lys Arg Ser Phe Phe Thr Ala Ala Gly Asp
            100                 105                 110

Asp Gly Asn Leu Val Thr Pro Tyr Gln Ala Arg Val Val Glu Leu Glu
        115                 120                 125

Ser Pro Glu Ala Ala Ala Glu Glu Ala Glu Ala
    130                 135

<210> SEQ ID NO 33
<211> LENGTH: 133
<212> TYPE: PRT
<213> ORGANISM: Saccharum sp.
<220> FEATURE:
<221> NAME/KEY: MOD_RES
<222> LOCATION: (115)..(115)
<223> OTHER INFORMATION: Any amino acid

<400> SEQUENCE: 33

Thr Ser Asn Ala Ala Thr Ala Lys Arg Pro Ala Gly Ser Ser Lys Val
1               5                   10                  15

Arg Val Val Pro Ser Arg Tyr Ser Ile Thr Pro Gly Ser Tyr Leu Ala
            20                  25                  30

Ala Val Ser Gln Asp Lys Arg Ser Lys Gln Ser Leu Pro Gly Pro Ala
        35                  40                  45

Ser Ala Ala Ser Gln Arg Glu Glu Ile Arg Ala Lys Leu Thr Glu Pro
50                  55                  60

Ser Lys Asp Glu Leu Ser Pro Glu Thr Val Lys Val Ala Glu Leu
65                  70                  75                  80

Leu Pro Arg Ile Lys Thr Met Pro Ala Ser Asp Glu Ser Pro Arg Asp
                85                  90                  95

Ser Ser Cys Ala Lys Arg Val Ala Asp Leu Val Gly Lys Arg Ser Phe
            100                 105                 110

Phe Thr Xaa Ala Ala Glu Asp Gly Asn Phe Val Thr Pro Tyr Gln Ala
            115                 120                 125

Pro Val Gly Glu Leu
        130

<210> SEQ ID NO 34
<211> LENGTH: 98
<212> TYPE: PRT
<213> ORGANISM: Pinus taeda
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (77)..(78)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (96)..(98)
<223> OTHER INFORMATION: Any amino acid

<400> SEQUENCE: 34

Xaa Glu Ala Arg Ile Val Phe Gly Thr Gly Asn Ser Ala Ile Met Ala
1               5                   10                  15

Gly Gly Thr Lys Ala Pro Asp Thr Leu Glu Arg His Lys Met Lys Leu
            20                  25                  30

Pro Lys Ile Lys Thr Val Arg Phe Thr Thr Glu Ser Pro Arg Asp Ser
        35                  40                  45

Gly Cys Ile Lys Arg Glu Ile Asp Arg Ile Gly Lys Lys Ser Phe Phe
    50                  55                  60

Ala Pro Asp Gly Ile Thr Ser Thr Pro Ser Ile Asp Xaa Xaa Asp Ala
65                  70                  75                  80

Gly Lys Pro Leu Arg Arg Glu Ser Val His Glu Ile Xaa His Ala Xaa
                85                  90                  95

Xaa Xaa

<210> SEQ ID NO 35
<211> LENGTH: 7
<212> TYPE: PRT

```
<213> ORGANISM: Artificial Sequence
<220> FEATURE:
<223> OTHER INFORMATION: Description of Artificial Sequence: Synthetic
      Motif 1 CORE peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 35

Trp Xaa Asn Ala Xaa Xaa Asp
1               5

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      Motif 3 (coiled core) CORE peptide
<220> FEATURE:
<221> NAME/KEY: MOD_RES
<222> LOCATION: (2)..(7)
<223> OTHER INFORMATION: Any amino acid and this region may encompass 1
      to 6 residues
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (17)..(18)
<223> OTHER INFORMATION: Any amino acid

<400> SEQUENCE: 36

Glu Xaa Xaa Xaa Xaa Xaa Xaa Glu Xaa Xaa Arg Leu Xaa Xaa Xaa Leu
1               5                   10                  15

Xaa Xaa Leu Arg
            20

<210> SEQ ID NO 37
<211> LENGTH: 29
<212> TYPE: PRT
<213> ORGANISM: Artificial Sequence
<220> FEATURE:
<223> OTHER INFORMATION: Description of Artificial Sequence: Synthetic
      Motif 4 CORE peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(14)
<223> OTHER INFORMATION: Any amino acid and this region may encompass 1
      to 10 residues
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (23)..(28)
<223> OTHER INFORMATION: Any amino acid and this region may encompass 1
      to 6 residues

<400> SEQUENCE: 37
```

```
Leu Pro Xaa Ile Xaa Xaa Xaa Xaa Xaa Xaa Xaa Xaa Xaa Arg Asp
1               5                   10                  15

Ser Gly Xaa Xaa Lys Arg Xaa Xaa Xaa Xaa Xaa Xaa Lys
            20              25
```

SEEDY 1 NUCLEIC ACIDS FOR MAKING PLANTS HAVING CHANGED GROWTH CHARACTERISTICS

FIELD OF THE INVENTION

The present invention concerns a method for modifying growth characteristics of a plant. More specifically, the present invention concerns a method for modifying growth characteristics of a plant by modifying expression of a seedy1 nucleic acid and/or by modifying levels and/or activity of a seedy1 protein in a plant. The present invention also concerns plants having modified growth characteristics and modified expression of a seedy1 nucleic acid and/or modified levels and/or activity of a seedy1 protein relative to corresponding wild type plants.

BACKGROUND OF THE INVENTION

The ever-increasing world population and the dwindling supply of arable land available for agriculture fuel research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits A trait of particular economic interest is yield. Yield is normally defined as the measurable produce of economic value from a crop. This may be defined in terms of quantity and/or quality. Crop yield may not only be increased by combating one or more stresses to which a crop or plant is typically subjected, but may also be increased by modifying the inherent growth characteristics of a plant. Yield is directly dependent on several growth characteristics, for example, growth rate, biomass production, plant architecture, number and size of organs, (for example, the number of branches, tillers, shoots, flowers), seed production and more. Root development and nutrient uptake may also be important factors in determining yield.

The ability to modify one or more plant growth characteristics, would have many applications in areas such as crop enhancement, plant breeding, production of ornamental plants, aboriculture, horticulture, forestry, production of algae or plants (for example for use as bioreactors, for the production of substances such as pharmaceuticals, antibodies, or vaccines, or for the bioconversion of organic waste or for use as fuel in the case of high-yielding algae and plants).

SUMMARY OF THE INVENTION

It has now been found that modifying expression in a plant of a seedy1 nucleic acid and/or modifying the level and/or activity in a plant of a seedy1 protein gives plants having modified growth characteristics relative to corresponding wild type plants.

A seedy1 protein is defined herein as being a protein comprising in the following order from N-terminus to C-terminus:

(i) a motif having at least 80% sequence identity to the sequence represented by SEQ ID NO 15; and
(ii) a motif having at least 80% sequence identity to the sequence represented by SEQ ID NO 16; and
(iii) a motif having at least 80% sequence identity to the sequence represented by SEQ ID NO 17, and which motif is a coiled coil motif; and
(iv) a motif having at least 80% sequence identity to the sequence represented by SEQ ID NO 18.

DETAILED DESCRIPTION OF THE INVENTION

A seedy1 nucleic acid/gene is defined herein as being a nucleic acid or gene encoding a seedy1 protein. The terms "seedy1 gene", "seedy1 nucleic acid" and "nucleic acid encoding a seedy1 protein" are used interchangeably herein. The term seedy1 nucleic acid/gene, as defined herein, also encompasses a complement of the sequence and corresponding RNA, DNA, cDNA or genomic DNA. The seedy1 nucleic acid may be synthesised in whole or in part and it may be a double-stranded nucleic acid or a single-stranded nucleic acid. The term also encompasses variants due to the degeneracy of the genetic code and variants that are interrupted by one or more intervening sequences.

A seedy1 nucleic acid/gene or a seedy1 protein may be wild type, i.e. a native or endogenous nucleic acid or protein. The nucleic acid may be derived from the same or another species, which nucleic acid is introduced as a transgene, for example by transformation. This transgene may be substantially changed from its native form in composition and/or genomic environment through deliberate human manipulation. The nucleic acid may thus be derived (either directly or indirectly (if subsequently modified)) from any source provided that the nucleic acid, when expressed in a plant, gives modified plant growth characteristics. The nucleic acid may be isolated from a microbial source, such as bacteria, yeast or fungi, or from a plant, algae, insect, or animal (including human) source. Preferably, the seedy1 nucleic acid is isolated from a plant. The nucleic acid may be isolated from a dicotyledonous species, preferably from the family Solanaceae, further preferably from Nicotiana. More preferably, the seedy1 nucleic acid encodes a seedy1 protein as defined hereinabove. Most preferably, the seedy1 nucleic acid is as represented by SEQ ID NO: 1, or by a portion thereof, or by a nucleic acid capable of hybridising with the sequence represented by SEQ ID NO: 1, or is a nucleic acid encoding an amino acid represented by SEQ ID NO: 2 or a homologue derivative or active fragment thereof, which homologue has in increasing order of preference at least 20%, 25%, 30%, 35%, 40%, 45%, 50%, 55%, 60%, 65%, 70%, 75%, 80%, 85%, 90%, 95% 98% or 99% sequence identity with the sequence represented by SEQ ID NO 2.

The present invention provides a method for modifying the growth characteristics of a plant, comprising modifying expression in a plant of a nucleic acid encoding a seedy1 protein and/or modifying the level and/or activity in a plant of a seedy1 protein, wherein said seedy1 protein comprises in the following order from N-terminus to C-terminus:

(i) a motif having at least 80% sequence identity to the sequence represented by SEQ ID NO 15; and
(ii) a motif having at least 80% sequence identity to the sequence represented by SEQ ID NO 16, and
(iii) a motif having at least 80% sequence identity to the sequence represented by SEQ ID NO 17 and which is a coiled coil motif; and
(iv) a motif having at least 80% sequence identity to the sequence represented by SEQ ID NO 18, wherein the growth characteristics are modified relative to the growth characteristics of corresponding wild-type plants.

The present invention also provides a hitherto unknown seedy1 protein, which seedy1 protein comprises in the following order from N-terminus to C-terminus:
- (i) a motif having at least 80% sequence identity to the sequence represented by SEQ ID NO 15; and
- (ii) a motif having at least 80% sequence identity to the sequence represented by SEQ ID NO 16; and
- (iii) a motif having at least 80% sequence identity to the sequence represented by SEQ ID NO 17 and which motif is a coiled coil motif; and
- (iv) a motif having at least 80% sequence identity to the sequence represented by SEQ ID NO 18, with the proviso that the seedy1 protein is not the *Arabidopsis* protein as deposited in Genbank under NCBI accession number AL161572 (SEQ ID NO 12).

According to a particular embodiment, the motif according to SEQ ID NO: 15 is as represented by: (P/X)X((V/L/H)(Q/H)(V/I)W(N/X)NA(A/P)(F/C)D, wherein X may be any amino acid and wherein
- (P/X) preferably is P or is A or T or Q or another amino acid
- (V/L/H) preferably is V or L or H
- (Q/H) is either Q or H
- (V/I) is either V or is T or S or another amino acid
- (A/P) is preferably A or is P
- (F/C) is preferably F or is C.

According to a particular embodiment, the motif according to SEQ ID NO 17 is as represented by: (I/V/A)(D/E)XE(I/M)XX(I/V)(E/Q)XE(I/X)XRL(S/X)(S/X)(R/K)LXXLR (L/V/T/I)X(K/Q), where X may be any amino acid and wherein:
- (I/V/A) preferably is I or V or is A
- (D/E) is either D or E
- (I/M) preferably is I or is M
- (I/V) preferably is I or is V
- (E/Q) preferably is E or is Q
- (I/X) preferably is I or is M or is V or any other amino acid
- (S/X) preferably S or is T or any other amino acid
- (S/X) preferably is S or is T or L or I or A
- (R/K) preferably is R or is K
- (L/V/T/I) preferably is L or T or V or I
- (K/Q) preferably is K or Q and which motif is a coiled coil motif.

According to a particular embodiment, the motif according to SEQ ID NO 18 is as represented by: LP(R/K)I(R/X)(T/I)(M/X)(P/R)XX(D/X)(E/G)(S/T)(P/L)RDSG(C/X)(A/X)KR (V/X)(A/I)(D/E) (L/R)(V/X)(G/A)K, where X may be any amino acid and wherein
- (R/K) is either R or K
- (R/X) is preferably R or is S or K
- (T/I) is preferably T or I
- (M/X) is preferably M or L or A or V
- (P/R) is either P or R
- (D/X) is preferably D or is G or T or N
- (E/G) is preferably E or is G
- (S/T) is preferably S or is T
- (P/L) is preferably P or is L
- (C/X) is preferably C or is P or A
- (A/X) is preferably A or is V or I
- (A/I) is preferably A or is I
- (D/E) is either D or E
- (L/R) is preferably L or is R
- (V/X) is preferably V or is Q or N or I
- (G/A) is preferably G or is A.

The present invention also provides a hitherto unknown isolated seedy1 nucleic acid/gene selected from:
- (i) a nucleic acid represented by any one of SEQ ID NO: 1, 5 or 7 or the complement of any of the aforementioned;
- (ii) a nucleic acid encoding an amino acid sequence represented by SEQ ID NO: 2, 4, 6, 8 or 10;
- (iii) a nucleic acid encoding a homologue, derivative or active fragment of (i) or (ii) above;
- (iv) a nucleic add capable of hybridising with a nucleic acid of (i), (ii) or (iii) above;
- (v) a nucleic acid which is degenerate as a result of the genetic code from any one of the nucleic acids of (i) to (iv) above;
- (vi) a nucleic acid which is an allelic variant of any one of the nucleic acids of (i) to (v) above;
- (vii) a nucleic acid which is an alternative splice variant of any one of the nucleic acids of (i) to (vi);
- (viii) a nucleic acid encoding a protein which has in increasing order of preference at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 75%, 80%, 85%, 90%, 95%, 96%, 97%, 98% or 99% sequence identity to any one or more from the sequences defined in (i) to (vii) above;
- (ix) a portion of a nucleic acid according to any of (i) to (viii) above;

wherein the nucleic acids of (i) to (ix) above encode a seedy1 protein as defined hereinabove, and with the proviso that the isolated nucleic acid is not a rice cDNA as deposited under Genbank accession number AK063941 (SEQ ID NO 3), a *Medicago* BAC clone deposited as AC144618, AC139356, AC144482 or AC135566, the *Arabidopsis* cDNA deposited under AL61572 (SEQ ID NO 11) or the *Zea mays* EST deposited under AY108162 (SEQ ID NO 9).

Modifying expression of a seedy1 nucleic acid and/or modifying activity and/or levels of a seedy1 protein may be effected by modifying expression of a gene and/or by modifying activity and/or levels of a gene product, namely a polypeptide, in specific cells or tissues. The term "modifying" as used herein (in the context of modifying expression, activity and/or levels) means increasing, decreasing or changing in time or place. The modified expression, activity and/or levels of a seedy1 gene or protein are modified compared to expression, activity and/or levels of a seedy1 gene or protein in corresponding wild-type plants. The modified gene expression may result from modified expression levels of an endogenous seedy1 gene and/or may result from modified expression levels of a seedy1 gene introduced into a plant. Similarly, levels and/or activity of a seedy1 protein may be modified due to modified expression of an endogenous seedy1 nucleic acid/gene and/or due to modified expression of a seedy1 nucleic acid/gene introduced into a plant. Activity of a seedy1 protein may be increased by increasing levels of the protein itself. Activity may also be increased without any increase in levels of a seedy1 protein or even when there is a reduction in levels of a seedy1 protein. This may occur when the intrinsic properties of the polypeptide are altered, for example, by making a mutant form that is more active than the wild type. Mutations may cause conformational changes in a protein, resulting in more activity and/or levels of a protein. Modified expression of a gene/nucleic acid and/or modifying activity and/or levels of a gene product/protein may be effected, for example, by introducing a genetic modification (preferably in the locus of a seedy1 gene). The locus of a gene as defined herein is taken to mean a genomic region which includes the gene of interest and 10KB up- or down stream of the coding region.

The genetic modification may be introduced, for example, by any one (or more) of the following methods: TDNA activation, tilling, site-directed mutagenesis, homologous recombination or by introducing and expressing in a plant a nucleic acid encoding a seedy1 protein or a homologue, derivative or active fragment thereof. Following introduction of the genetic modification, there follows a step of selecting for increased expression and/or activity and/or levels of a seedy1 protein, which increase in expression and/or activity and/or levels gives plants having modified growth characteristics.

T-DNA activation tagging (Hayashi et al. Science (1992) 1350-1353) involves insertion of T-DNA usually containing a promoter (may also be a translation enhancer or an intron), in the genomic region of the gene of interest or 10KB up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a seedy1 gene using the technique of TILLING (Targeted Induced Local Lesions IN Genomes). This is a mutagenesis technology useful to generate and/or identify, and to isolate mutagenised variants of a seedy1 nucleic acid. TILLING also allows selection of plants carrying such mutant variants. These mutant variants may even exhibit higher seedy1 activity than exhibited by the gene in its natural form. TILLING combines high-density mutagenesis with high-throughput screening methods. The steps typically followed in TILLING are: (a) EMS mutagenesis (Redei and Koncz, 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (9) sequencing of the mutant PCR product. Methods for TILLING are well known in the art (McCallum Nat Biotechnol. 2000 April; 18(4): 455-7, reviewed by Stemple 2004 (TILLING—A high-throughput harvest for functional genomics. Nat Rev Genet. 2004 February; 5(2):145-50)).

Site directed mutagenesis may be used to generate variants of seedy1 nucleic acids or portions thereof. Several methods are available to achieve site directed mutagenesis; the most common being PCR based methods (current protocols in molecular biology. Wiley Eds. <4ulr.com/products/current-protocols/index.html>.

TDNA activation, TILLING and site-directed mutagenesis are examples of technologies that enable the generation of novel alleles and seedy1 nucleic acid variants that are therefore useful in the methods of the invention.

Homologous recombination allows introduction in a genome of a selected nucleic acid at a defined selected position. Homologous recombination is a standard technology used routinely in the biological sciences for lower organisms such as yeast or moss (e.g. *physcomitrella*). Methods for performing homologous recombination in plants have been described not only for model plants (Offring a et al. Extrachromosomal homologous recombination and gene targeting in plant cells after *Agrobacterium*-mediated transformation, 1990 EMBO J. 1990 October; 9(10):3077-84) but also for crop plants, for example rice (Terada R. Urawa H, Inagaki Y. Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. 2004 April; 15(2):132-8). The nucleic acid to be targeted need not be targeted to the locus of a seedy1 gene, but may be introduced in, for example, regions of high expression. The nucleic acid to be targeted may be an improved allele used to replace the endogenous gene or may be introduced in addition to the endogenous gene.

A preferred method for introducing a genetic modification is to introduce and express in a plant a seedy1 nucleic acid/gene or a portion thereof, or sequences capable of hybridising with the seedy1 nucleic acid/gene, which nucleic acid encodes a seedy1 protein or a homologue, derivative or active fragment thereof. In this case, the genetic modification need not be in the locus of a seedy1 gene. The nucleic acid may be introduced into a plant by, for example, transformation.

Accordingly, the present invention provides a method for modifying the growth characteristics of a plant, comprising introducing and expressing in a plant a seedy1 nucleic acid/gene or a portion thereof, or sequences capable of hybridising with the seedy1 nucleic acid/gene, which nucleic acid encodes a seedy1 protein or a homologue, derivative or active fragment thereof.

Advantageously, the methods according to the invention may also be practised using variant nucleic acids and variant amino acids of SEQ ID NO 1 or 2 respectively. The term seedy1 nucleic acid or seedy1 protein encompasses variant nucleic acids and variant amino acids. The variant nucleic acids encode seedy1 proteins as defined hereinabove, i.e. those comprising in the following order from N-terminus to C-terminus:
  (i) a motif having at least 80% sequence identity to the sequence represented by SEQ ID NO 15; and
  (ii) a motif having at least 80% sequence identity to the sequence represented by SEQ ID NO 16; and
  (iii) a motif having at least 80% sequence identity to the sequence represented by SEQ ID NO 17, and which motif is a coiled coil motif; and
  (iv) a motif having at least 80% sequence identity to the sequence represented by SEQ ID NO 18,
and variant seedy1 proteins are those comprising in the following order from N-terminus to C-terminus:
  (i) a motif having at least 80% sequence identity to the sequence represented by SEQ ID NO 15; and
  (ii) a motif having at least 80% sequence identity to the sequence represented by SEQ ID NO 16; and
  (iii) a motif having at least 80% sequence identity to the sequence represented by SEQ ID NO 17, and which motif is a coiled coil motif; and
  (iv) a motif having at least 80% sequence identity to the sequence represented by SEQ ID NO 18.

Suitable variant nucleic acid and amino acid sequences useful in practising the method according to the invention, include:
  (i) Portions of a seedy1 nucleic acid/gene;
  (ii) Sequences capable of hybridising with a seedy1 nucleic acid/gene;
  (iii) Alternative splice variants of a seedy1 nucleic acid/gene;

(iv) Allelic variants of a seedy1 nucleic acid/gene;
(v) Homologues, derivatives and active fragments of a seedy1 protein.

An example of a variant seedy1 nucleic acid is a portion of a seedy1 nucleic acid. The methods according to the invention may advantageously be practised using functional portions of a seedy1 nucleic acid. A portion refers to a piece of DNA derived or prepared from an original (larger) DNA molecule, which DNA portion, when introduced and expressed in a plant, gives plants having modified growth characteristics and which portion encodes a seedy1 protein as defined hereinabove. The portion may comprise many genes, with or without additional control elements or may contain spacer sequences. The portion may be made by making one or more deletions and/or truncations to the nucleic acid. Techniques for introducing truncations and deletions into a nucleic acid are well known in the art. Portions suitable for use in the methods according to the invention may readily be determined by following the methods described in the Examples section by simply substituting the sequence used in the actual Example with the portion to be tested for functionality.

An example of a further variant seedy1 nucleic acid is a sequence that is capable of hybridising to a seedy1 nucleic acid as defined hereinabove, for example to a seedy1 nucleic acid as represented by any one of SEQ ID NO 1, 3, 5, 7, 9 or 11. Such hybridising sequences are those encoding a seedy1 protein as defined hereinabove. Hybridising sequences suitable for use in the methods according to the invention may readily be determined for example by following the methods described in the Examples section by simply substituting the sequence used in the actual Example with the hybridising sequence.

The term "hybridisation" as defined herein is a process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and Na$_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid. Sufficiently low stringency hybridisation conditions are particularly preferred (at least in the first instance) to isolate nucleic acids heterologous to the DNA sequences of the invention defined supra. An example of low stringency conditions is 4-6×SSC/0.1-0.5% w/v SDS at 37-45° C. for 2-3 hours. Depending on the source and concentration of the nucleic acid involved in the hybridization, alternative conditions of stringency may be employed, such as medium stringency conditions. Examples of medium stringency conditions include 1-4×SSC/0.25% w/v SDS at ≧45° C. for 2-3 hours. An example of high stringency conditions includes 0.1-1×SSC 10.1% w/v SDS at 60° C. for 1-3 hours. The skilled man will be aware of various parameters which may be altered during hybridisation and washing and which will either maintain or change the stringency conditions. The stringency conditions may start low and be progressively increased until there is provided a hybridising seedy1 nucleic acid, as defined hereinabove. Elements contributing to heterology include allelism, degeneration of the genetic code and differences in preferred codon usage.

Another example of a variant seedy1 is an alternative splice variant of a seedy1 nucleic acid/gene. The methods according to the present invention may also be practised using an alternative splice variant of a seedy1 nucleic acid. The term "alternative splice variant" as used herein encompasses variants of a nucleic acid in which selected introns and/or exons have been excised, replaced or added. Such splice variants may be found in nature or can be manmade using techniques well known in the art. Preferably, the splice variant is a splice variant of a sequence represented by any of SEQ ID NO 1, 3, 5, 7, 9 or 11. Splice variants suitable for use in the methods according to the invention may readily be determined for example by following the methods described in the Examples section by simply substituting the sequence used in the actual Example with the splice variant.

Another example of a variant seedy1 is an allelic variant. Advantageously, the methods according to the present invention may also be practised using allelic variants of a seedy1 nucleic acid, preferably an allelic variant of a seedy1 nucleic acid sequence represented by any of SEQ ID NO 1, 3, 5, 7, 9 or 11. Allelic variants exist in nature and encompassed within the methods of the present invention is the use of these isolated natural alleles in the methods according to the invention. Allelic variants encompass Single Nucleotide Polymorphisms (SNPs), as well as Small Insertion/Deletion Polymorphisms (INDELs). The size of INDELs is usually less than 100 bp). SNPs and INDELs form the largest set of sequence variants in naturally occurring polymorphic strains of most organisms. Allelic variants suitable for use in the methods according to the invention may readily be determined for example by following the methods described in the Examples section by simply substituting the sequence used in the actual Example with the allelic variant.

Examples of variant seedy1 amino acids include homologues, derivatives and active fragments of a seedy1 protein, preferably of a seedy1 protein as represented by any one of SEQ ID NO 2, 4, 6, 8, 10 or 12. Homologues, derivatives and active fragments of a seedy1 protein are those comprising in the following order from N-terminus to C-terminus:

(i) a motif having at least 80% sequence identity to the sequence represented by SEQ ID NO 15; and
(ii) a motif having at least 80% sequence identity to the sequence represented by SEQ ID NO 16; and
(iii) a motif having at least 80% sequence identity to the sequence represented by SEQ ID NO 17, and which motif is a coiled coil motif; and
(iv) a motif having at least 80% sequence identity to the sequence represented by SEQ ID NO 18.

Preferred seedy1 homologues, derivatives and active fragments have a coiled coil domain, preferably located in the N-terminal half of the protein, more preferably between amino acid position 25 to 250, more preferably between position 50 and 150. A coiled coil domain typically determines protein folding.

"Homologues" of a seedy1 protein encompass peptides, oligopeptides, polypeptides, proteins and enzymes having amino acid substitutions, deletions and/or insertions relative to the unchanged protein in question and having similar biological and functional activity as the unchanged protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

The homologues of a seedy1 protein have a percentage identity to any one of SEQ ID NO 2, 4, 6, 8, 10 or 12 equal to a value lying between 20% and 99.99%, i.e. in increasing order of preference at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% sequence identity or similarity (functional identity) to the unchanged protein, alternatively at least 60% sequence identity or similarity to an unchanged protein, alternatively at least 70% sequence identity or similarity to an unchanged protein. Typically, the homologues have at least 75% or 80% sequence identity or similarity to an unchanged protein, preferably at least 85%, 86%, 87%, 88%, 89% sequence identity or similarity, further preferably at least 90%, 91%, 92%, 93%, 94% sequence identity or similarity to an unchanged protein, most preferably at least 95%, 96%, 97%, 98% or 99% sequence identity or similarity to an unchanged protein. The percentage identities are when comparing full-length sequences. Homologues suitable for use in the methods according to the invention may readily be determined for example by following the methods described in the Examples section by simply substituting the sequence used in the actual Example with the homologous sequence.

Percentage identity may be calculated using an alignment program, such alignment programs being well known in the art. For example, percentage identity may be calculated using the program GAP, or needle (EMBOSS package) or stretcher (EMBOSS package) or the program align X, as a module of the vector NTI suite 5.5 software package, using the standard parameters (for example GAP penalty 5, GAP opening penalty 15, GAP extension penalty 6.6).

Methods for the search and identification of seedy1 homologues or DNA sequences encoding a seedy1 homologue, would be well within the realm of persons skilled in the art. Such methods, involve screening sequence databases with the sequences as provided by the present invention in SEQ ID NO 1 and 2 or 3 to 10, preferably a computer readable format of the nucleic acids of the present invention. This sequence information is available for example in public databases, that include but are not limited to Genbank (<ncbi.nlm.nih.gov/web/Genbank>), the European Molecular Biology Laboratory Nucleic acid Database (EMBL) (<ebi.ac.uk/ebi-docs/embl-db.html>) or versions thereof or the MIPS database (<mips.gsf.de>). Different search algorithms and software for the alignment and comparison of sequences are well known in the art. Such software includes GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percentage sequence identity and performs a statistical analysis of the similarity between the two sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., GenomeAnalysis, 1: 543, 1997). The software for performing BLAST analysis is publicly available through the National Centre for Biotechnology Information.

Homologues of SEQ ID NO 2 may be found in many different organisms. The closest homologues are found in the plant kingdom. For example, seedy1 proteins were isolated from tobacco (SEQ ID NO 2), rice (SEQ ID NO 4), medicago (SEQ ID NO 6), sugar cane (SEQ ID NO 8), maize (SEQ ID NO 10) and from *Arabidopsis* (SEQ ID NO 12). Furthermore, ESTs from other organisms have been deposited in Genbank, for example an EST from *Vitis vinifera* (accession number CA816066), from *Pinus taeda* (accession number BM903108), from *Saccharus* sp. (accession numbers CA228193 and CA256020), from *Citrus sinsensis* (accession number CF833583), *Plumbago zeylanica* (accession number CB817788), from *Zea mays* (accession number CF637447, AW282224, CD058812, AY108162, CD059048, CF041861, AW067243), from *Triticum aestivum* (CA727065, BJ264506, BJ259034), from *Hordeum vulgare* (accession number BU997034, CA727065, CA031127, BQ762011), from *Brassica napus* (CD817460) from *Gossypium arboreum* (BG446106, BM360339), from *Eschscholzia californica* (CD478368), from *Populus tremula* (BU821376) and from *Beta vulgaris* (BQ594009). As more genomes are sequenced, many more seedy1 homologues will be identified.

The identification of domains or motifs, would also be well within the realm of a person skilled in the art and involves for example, a computer readable format of the nucleic acids of the present invention, the use of alignment software programs and the use of publicly available information on protein domains, conserved motifs and boxes. This protein domain information is available in the PRODOM (<biochem.ucl.ac.uk/bsm/dbbrowser/jj/prodomsrchjj.html>) PIR (<pir.georgetown.edu>) or pFAM (<pfam.wustl.edu>) database. Sequence analysis programs designed for motif searching may be used for identification of fragments, regions and conserved domains as mentioned above. Preferred computer programs would include but are not limited to MEME, SIGNALSCAN, and GENESCAN. A MEME algorithm (Version 3.0) can be found in the GCG package; or on the Internet site <sdsc.edu/MEME/mem>SIGNALSCAN version 4.0 information is available on the Internet site <biosci.cbs.umn.edu/software/sigscan.htlm>GENESCAN can be found on the Internet site <genomic.stanford.edu/GENESCANW.html>.

Two special forms of homology, orthologous and paralogous, are evolutionary concepts used to describe ancestral relationships of genes. The term "paralogous" relates to gene-duplications within the genome of a species. The term "orthologous" relates to homologous genes in different organisms due to ancestral relationship and the formation of different species. The term "homologue" as defined herein also encompasses paralogues and orthologues.

Orthologues in, for example, monocot plant species may easily be found by performing a so called reciprocal blast search. This may be done by a first blast involving blasting the sequence in question (for example, SEQ ID NO: 1 or SEQ ID NO: 2) against any sequence database, such as the publicly available NCBI database which may be found at: <ncbi.nlm.nig.gov>. If orthologues in rice were sought, the sequence in question would be blasted against, for example, the 28,469 full-length cDNA clones from Oryza sativa Nipponbare available at NCBI. BLASTn or tBLASTX may be used when starting from nucleotides or BLASTP or TBLASTN when starting from the protein, with standard default values. The blast results may be filtered. The full-length sequences of either the filtered results or the non-filtered results are then blasted back (second blast) against the sequences of the organism from which the sequence in question is derived. The results of the first and second blasts are then compared. An orthologue is found when the results of the second blast give as hits with the highest similarity a seedy1 nucleic acid or protein; if one of the organisms is tobacco then a paralogue is found. In the case of large families, ClustalW may be used, followed by a neighbour joining tree, to help visualize the clustering.

Example homologues of a seedy1 protein according to SEQ ID NO: 2 include a seedy1 protein as represented by SEQ ID NO 4 (rice), SEQ ID NO 8 (sugar cane) and SEQ ID NO 10 (maize), SEQ ID NO 6 (medicago) and SEQ ID NO 12 (*Arabidopsis*). The proteins represented by SEQ ID NO 8 (sugar cane) and SEQ ID NO 10 (Maize) are only partial, but the corresponding full length sequences of the proteins and encoding cDNA may easily be determined by a person skilled in the art using routine techniques, such as colony hybridization of a cDNA library or using PCR based on the use of specific primers combined with degenerate primers.

Another variant of seedy1 useful in the methods of the present invention is a derivative of seedy1. The term "derivatives" refers to peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a seedy1 protein encompass peptides, oligopeptides, polypeptides, proteins and enzymes which may comprise naturally occurring changed, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence such as, for example, a reporter molecule which is bound to facilitate its detection, andnon-naturally occurring amino acid residues relative to the amino acid sequence of a naturally occurring protein.

"Substitutional variants" of a protein are those in which at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues, and deletions will range from about 1 to 20 residues. Preferably, amino acid substitutions comprise conservative amino acid substitutions.

"Insertional variants" of a protein are those in which one or more amino acid residues are introduced into a predetermined site in a protein. Insertions can comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag (SEO ID NO: 19), glutathione S-transferase-tag, protein A, maltose-binding protein, dihydrofolate reductase, Tag·100 epitope, c-myc epitope, FLAG®-epitope, lacZ, CMP (calmodulin-binding peptide), HA epitope, protein C epitope and VSV epitope.

"Deletion variants" of a protein are characterised by the removal of one or more amino acids from the protein. Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif), PCR-mediated site-directed mutagenesis or other site-directed mutagenesis protocols.

Another variant of a seedy1 protein/amino acid useful in the methods of the present invention is an active fragment of a seedy1 protein. "Active fragments" of a seedy1 protein encompass contiguous amino acid residues of a seedy1 protein, which residues retain similar biological and/or functional activity to the naturally occurring protein. Useful fragments are those falling within the definition of a seedy1 protein as defined hereinabove. Preferably, the fragments start at one of the second or third or further internal methionine residues. These fragments originate from protein translation, starting at internal ATG codons.

For determining the presence of conserved motifs, sequences are aligned using suitable software, such as Align X or dustal X, for indication of the conserved residues (see for example FIG. 3). Software packages like MEME version 3.0 may also be used to determine motifs in sequences. This software is available from UCSD, SDSC and NBCR at http://meme.sdsc.edu/meme/. For the identification of a coiled coil domain, the software Coils 2.0 can be used. This software is available at http://www.ch.embnet.orq/software/COILS form.html. The 'X' in the motifs represented by SEQ ID NO 15, 16, 17 and 18 represents any amino acid.

According to a preferred aspect of the present invention, enhanced or increased expression of a seedy1 nucleic acid in a plant or plant part is envisaged. Methods for obtaining increased expression of genes or gene products are well documented in the art and indude, for example, overexpression driven by a (strong) promoter, the use of transcription enhancers or translation enhancers. The term overexpression as used herein means any form of expression that is additional to the original wild-type expression level. Preferably the seedy1 nudeic acid is in the sense direction with respect to the promoter to which it is operably linked. Alternatively, selection of better performing alleles of the wild-type seedy1 nudeic acid can be achieved via plant breeding techniques.

The expression of a seedy1 gene may be investigated by Northern or Southern blot analysis of cell extracts. The levels of a seedy1 protein in cells may be investigated using Western blot analysis of cell extracts.

According to a further embodiment of the present invention, genetic constructs and vectors to facilitate introduction and/or expression of the nucleotide sequences useful in the methods according to the invention are provided. Therefore, the present invention provides a genetic construct comprising:

(i) A seedy1 nucleic acid encoding a seedy1 protein as defined hereinabove;
(ii) one or more control sequences capable of regulating expression of the nucleic acid of (i); and optionally
(iii) a transcription termination sequence.

According to methods of the present invention, such a genetic construct is introduced into a plant or plant part.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

The genetic construct may be an expression vector wherein said nucleic acid is operably linked to one or more control sequences allowing expression in prokaryotic and/or eukaryotic host cells.

The nucleic acid according to (i) may be any seedy1 nucleic acid as defined hereinabove, preferably a seedy1 nucleic acid as represented by any one of SEQ ID NO 1, 3, 5, 7, 9 or 11. The control sequence of (ii) is preferably a seed-preferred promoter, for example a prolamin promoter.

Plants are transformed with a vector comprising the sequence of interest, which sequence is operably linked to one or more control sequences (at least a promoter). The terms "regulatory element", "control sequence" are all used interchangeably herein and are to be taken in a broad context to refer to regulatory nucleic acids capable of effecting expression of the aforementioned terms are promoters. A "Promoter" encompasses transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the seedy1 nucleic acid. Preferably, the nucleic acid capable of modifying expression of a seedy1 gene is operably linked to a plant-derived promoter, preferably a plant-derived tissue-preferred promoter. The term "tissue-preferred" as defined herein refers to a promoter that is expressed predominantly in at least one tissue or organ. Preferably, the tissue-preferred promoter is a seed-preferred promoter or a seed-specific promoter, further preferably an endosperm-preferred promoter, more preferably a promoter isolated from a gene encoding a seed-storage protein, most preferably a promoter isolated from a prolamin gene, such as a rice prolamin promoter as represented by SEQ ID NO 14 or a promoter of similar strength and/or a promoter with a similar expression pattern as the rice prolamin promoter. Similar strength and/or similar expression pattern may be analysed, for example, by coupling the promoters to a reporter gene and checking the function of the reporter gene in tissues of the plant. One well-known reporter gene is beta-glucuronidase and the calorimetric GUS stain used to visualize beta-glucuronidase activity in plant tissue.

Examples of preferred seed-specific promoters and other tissue-specific promoters are presented in Table A, which promoters or derivatives thereof are useful in performing the methods of the present invention.

TABLE A

EXAMPLES OF SEED-PREFERRED PROMOTERS FOR USE IN THE PRESENT INVENTION

| GENE SOURCE | EXPRESSION PATTERN | REFERENCE |
| --- | --- | --- |
| seed-specific genes | seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| zein | seed | Matzke et al Plant Mol Biol, 14(3): 323-32 1990 |
| napA | seed | Stalberg, et al, Planta 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadins | endosperm | EMBO 3: 1409-15, 1984 |
| barley Itr1 promoter | endosperm | |

TABLE A-continued

EXAMPLES OF SEED-PREFERRED PROMOTERS
FOR USE IN THE PRESENT INVENTION

| GENE SOURCE | EXPRESSION PATTERN | REFERENCE |
|---|---|---|
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice α-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| sorgum γ-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |
| Metallothionein Mte, PRO0001 | transfer layer of embryo + calli | |
| putative beta-amylase, PRO0005 | transfer layer of embryo | |
| putative cellulose synthase, PRO0009 | weak in roots | |
| lipase (putative), PRO0012 | | |
| transferase (putative), PRO0014 | | |
| peptidyl prolyl cis-trans isomerase (putative), PRO0016 | | |
| Unknown, PRO0019 | | |
| prp protein (putative), PRO0020 | | |
| noduline (putative), PRO0029 | | |
| proteinase inhibitor Rgpi9, PRO0058 | seed | |
| beta expansine EXPB9, PRO0061 | weak in young flowers | |
| structural protein, PRO0063 | young tissues + calli + embryo | |
| xylosidase (putative), PRO0069 | | |
| prolamine 10 Kda, PRO0075 | strong in endosperm | |
| allergen RA2, PRO0076 | strong in endosperm | |
| prolamine RP7, PRO0077 | strong in endosperm | |
| CBP80, PRO0078 | | |
| starch branching enzyme I, PRO0079 | | |
| Metallothioneine-like ML2, PRO0080 | transfer layer of embryo + calli | |
| putative caffeoyl-CoA 3-O-methyltransferase, PRO0081 | shoot | |
| prolamine RM9, PRO0087 | strong in endosperm | |
| prolamine RP6, PRO0090 | strong endosperm | |
| prolamine RP5, PRO0091 | strong in endosperm | |
| allergen RA5, PRO0092 | | |
| putative methionine aminopeptidase, PRO0095 | embryo | |
| ras-related GTP binding protein, PRO0098 | | |
| beta expansine EXPB1, PRO0104 | | |
| Glycine rich protein, PRO0105 | | |
| metallothionein like protein (putative), PRO0108 | | |
| metallothioneine (putative), PRO0109 | | |
| RCc3, PRO0110 | strong root | |
| uclacyanin 3-like protein, PRO0111 | weak discrimination center/shoot meristem | |
| 26S proteasome regulatory particle non-ATPase subunit 11, PRO0116 | very weak meristem specific | |
| putative 40S ribosomal protein, PRO0117 | weak in endosperm | |
| chlorophyll a/b-binding protein presursor (Cab27), PRO0122 | very weak in shoot | |
| putative protochlorophyllide reductase, PRO0123 | strong leaves | |
| metallothionein RiCMT, PRO0126 | strong discrimination center/shoot meristem | |
| GOS2, PRO0129 | strong constitutive | |
| GOS9, PRO0131 | | |
| chitinase Cht-3, PRO0133 | very weak meristem specific | |
| alpha-globulin, PRO0135 | strong in endosperm | |
| alanine aminotransferase, PRO0136 | weak in endosperm | |
| cyclin A2, PRO0138 | | |
| Cyclin D2, PRO0139 | | |
| Cyclin D3, PRO0140 | | |
| cyclophyllin 2, PRO0141 | shoot and seed | |
| sucrose synthase SS1 (barley), PRO0146 | medium constitutive | |
| trypsin inhibitor ITR1 (barley), PRO0147 | weak in endosperm | |

TABLE A-continued

EXAMPLES OF SEED-PREFERRED PROMOTERS
FOR USE IN THE PRESENT INVENTION

| GENE SOURCE | EXPRESSION PATTERN | REFERENCE |
|---|---|---|
| ubiquitine 2 with intron, PRO0149 | strong constitutive | |
| WSI18, PRO0151 | embryo + stress | |
| HVA22 homologue (putative), PRO0156 | | |
| EL2, PRO0157 | | |
| Aquaporine, PRO0169 | medium constitutive in young plants | |
| High mobility group protein, PRO0170 | strong constitutive | |
| reversibly glycosylated protein RGP1, PRO0171 | weak constitutive | |
| cytosolic MDH, PRO0173 | shoot | |
| RAB21, PRO0175 | embryo + stress | |
| CDPK7, PRO0176 | | |
| Cdc2-1, PRO0177 | very weak in meristem | |
| sucrose synthase 3, PRO0197 | | |
| OsVP1, PRO0198 | | |
| OSH1, PRO0200 | very weak in young plant meristem | |
| putative chlorophyllase, PRO0208 | | |
| OsNRT1, PRO0210 | | |
| EXP3, PRO0211 | | |
| phosphate transporter OjPT1, PRO0216 | | |
| oleosin 18 kd, PRO0218 | aleurone + embryo | |
| ubiquitine 2 without intron, PRO0219 | | |
| RFL, PRO0220 | | |
| maize UBI delta intron, PRO0221 | | |
| glutelin-1, PRO0223 | | |
| fragment of prolamin RP6 promoter, PRO0224 | | |
| 4xABRE, PRO0225 | | |
| glutelin OSGLUA3, PRO0226 | | |
| BLZ-2_short (barley), PRO0227 | | |
| BLZ-2_long (barley), PRO0228 | | |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences, which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

In a preferred embodiment, the genetic construct comprises a prolamin promoter from rice operably linked to a seedy1 nucleic acid in the sense orientation. An example of such an expression cassette, further comprising a terminator sequence, is as represented by SEQ ID NO 13.

According to a further embodiment of the present invention, there is provided a method for the production of a plant having modified growth characteristics, comprising modifying expression and or activity and/or levels in a plant of a seedy1 nucleic acid or seedy1 protein.

According to a particular embodiment, the present invention provides a method for the production of a transgenic plant having modified growth characteristics, which method comprises:
 (i) introducing into a plant or plant part a seedy1 nucleic acid encoding a seedy1 protein;
 (ii) cultivating the plant cell under conditions promoting regeneration and mature plant growth.

The nucleic acid of (i) may advantageously be any of the aforementioned seedy1 nucleic acids.

The protein itself and/or the nucleic acid itself may be introduced directly into a plant cell or into the plant itself (including introduction into a tissue, organ or any other part of the plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g. cotyledon meristem and hypocotyl meristem). The polynucleotide may be transiently or stably introduced into a host cell and may be maintained non-integrated, for example, as a plasmid. Alternatively and preferably, the transgene may be stably integrated into the host genome. The resulting transformed plant cell can then be used to regenerate a transformed plant in a manner known to persons skilled in the art.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like.

Transgenic rice plants expressing a seedy1 gene are preferably produced via *Agrobacterium*-mediated transformation using any of the well known methods for rice transformation, such as described in any of the following: published European patent application EP 1198985 A1, Aldemita and Hodges (Planta, 199, 612-617, 1996); Chan et al. (Plant Mol. Biol. 22 (3) 491-506, 1993), Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant. Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention also encompasses plants obtainable by the methods according to the present invention. The present invention therefore provides plants obtainable by the method according to the present invention, which plants have modified growth characteristics, when compared to wild-type plants.

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention i.e. having modified growth characteristics.

The invention accordingly also includes host cells comprising an isolated seedy1 nucleic acid as defined hereinabove. Preferred host cells according to the invention are plant cells or cells from insects, animals, yeast, fungi, algae or bacteria. The invention also extends to harvestable parts of a plant, such as but not limited to seeds, flowers, stamen, leaves, petals, fruits, stem, stem cultures, rhizomes, roots, tubers and bulbs.

The term "plant" as used herein encompasses whole plants, ancestors and progeny of the plants and plant parts, including seeds, shoots, stems, roots (including tubers), and plant cells, tissues and organs. The term "plant" also therefore encompasses suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, Pinus spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea, trees. Alternatively algae and other non-Viridiplantae can be used for the methods of the present invention. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, millet, rye, sorghum or oats.

Advantageously, the present invention provides a method for modifying growth characteristics of a plant, which modified growth characteristics are selected from any one or more of increased yield, increased biomass, modified plant architecture.

Further preferably, increased yield is increased seed yield.

The term "increased yield" encompasses an increase in biomass in one or more harvestable parts of a plant relative to the total biomass of corresponding wild-type plants. The term also encompasses an increase in seed yield, which includes an increase in the biomass of the seed (seed weight) and/or an increase in the number of (filled) seeds and/or in the size of the seeds and/or an increase in seed volume, each relative to corresponding wild-type plants. An increase in seed size and/or volume may also influence the composition of seeds. An increase in seed yield could be due to an increase in the number and/or size of flowers. An increase in yield might also increase the harvest index, which is expressed as a ratio of the total biomass over the yield of harvestable parts, such as seeds.

The methods of the present invention are used to increase the seed yield of the plant and are therefore particularly favourable to be applied to crop plants, preferably seed crops and cereals. Therefore, the methods of the present invention are particularly useful for plants such as, rapeseed, sunflower, leguminosae (e.g. soybean, pea, bean) flax, lupinus, canola and cereals such as rice, maize, wheat, barley, millet, oats and rye.

Further preferably, increased biomass encompasses increased biomass of aboveground plant tissue, herein determined as aboveground plant area.

Additionally or alternatively, the plants according to the invention have increased aboveground area relative to corresponding wild type plants.

Further preferably, said modified plant architecture encompasses increased number of panicles and increased biomass relative to corresponding wild type plants.

The present invention also relates to use of a seedy1 nucleic acid and/or protein in modifying plant growth characteristics.

According to another aspect of the present invention, the seedy1 nucleic acid and/or seedy1 protein may be used in breeding programmes. In an example of such a breeding programme, a DNA marker is identified which may be genetically linked to a seedy1 nucleic acid/gene. This DNA marker may then be used in breeding programs to select plants having modified growth characteristics relative to corresponding wild type plants.

The methods according to the present invention result in plants having modified growth characteristics, as described hereinbefore. These advantageous characteristics may also be combined with other economically advantageous traits, such as further yield-enhancing traits, tolerance to various stresses, traits modifying various architectural features and/or biochemical and/or physiological features.

DESCRIPTION OF THE FIGURES

The present invention will now be described with reference to the following figures in which:

FIG. 3 shows an N-terminal and C-terminal alignment of seedy1 amino acids and deduced amino acids from ESTs, all from plants. This alignment was made with the program Align X of the VNTI software package. Motifs 1, 2, 3 and 4 are indicated with a bar. FIG. 3. page 2 discloses "CDS0689" as residues 1-154 of SEQ ID NO: 2, "CDS0689 At" as residues 1-126 of SEQ ID NO: 12. "CDS0689 Medicago truncatulata" as residues 1-88 of SEO ID NO: 6, "CDS0689 Os" as residues 1-89 of SEQ ID NO: 4, "CDS0689 Ta variant" as SEQ ID NO: 21, "CDS0689 So" as residues 1-85 of SEQ ID NO: 8 and the remaining sequences in FIG. 3, page 2 as SEQ ID NOS 22-29, respectively, in order of appearance. FIG. 3, page 3 discloses "CDS0689" as residues 339-475 of SEQ ID NO: 2, "CDS0689 At" as residues 294-402 of SEO ID NO: 12, "CDS0689 Medicago trunculata" as residues 284-394 of SEQ ID NO: 6, "CDS0689 Os" as residues 297-431 of SEO ID NO: 4 and the remaining sequences in FIG. 3, page 3 as SEQ ID NOS 30-34, respectively, in order of appearance.

FIG. 4 is the representation of nucleic acids, protein and motif sequences according to the invention.

EXAMPLES

Figure 1:
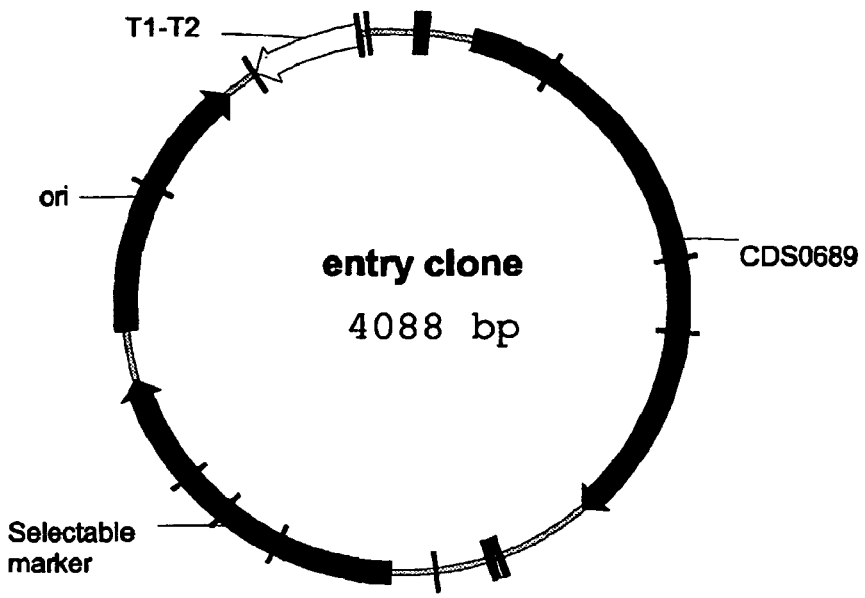
FIG. 1 is a schematic presentation of the entry done, containing CDS0689 within the AttL1 and AttL2 sites for Gateway® cloning in the pDONR201 backbone. CDS0689 is the internal code for the *Nicotiana tabacum* BY2 CDS0689 seedy1 coding sequence. This vector contains also a bacterial kanamycine-resistance cassette and a bacterial origin of replication.

The present invention will now be described with reference to the following examples, which are by way of illustration alone.

Unless otherwise stated, recombinant DNA techniques were performed according to standard protocols described in Sambrook (2001) Molecular Cloning: a laboratory manual, 3rd Edition Cold Spring Harbor Laboratory Press, CSH, New York; or in Volumes 1 and 2 of Ausubel et al. (1988), Current Protocols in Molecular Biology. Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Cloning of the Seedy1 Encoding Gene

A cDNA-AFLP experiment was performed on a synchronized tobacco BY2 cell culture (*Nicotiana tabacum* L. cv. Bright Yellow-2), and BY2 expressed sequence tags that were cell cycle modulated were identified and elected for further cloning. Subsequently, the expressed sequence tags were used to screen a tobacco cDNA library and to isolate the full-length cDNA of interest, namely the cDNA coding for the seedy1 protein of the present invention (CDS0689).
Synchronization of BY2 Cells.

Tobacco BY2 (*Nicotiana tabacum* L. cv. Bright Yellow-2) cultured cell suspension was synchronized by blocking cells in early S-phase with aphidicolin as follows. Cultured cell suspension of *Nicotiana tabacum* L. cv. Bright Yellow 2 were maintained as described (Nagata et al. Int. Rev. Cytol. 132, 1-30, 1992). For synchronization, a 7-day-old stationary culture was diluted 10-fold in fresh medium supplemented with aphidicolin (Sigma-Aldrich, St. Louis, Mo.; 5 mg/l), a DNA-polymerase a inhibiting drug. After 24 h, cells were released from the block by several washings with fresh medium and resumed their cell cycle progression.
RNA extraction and cDNA synthesis.

Total RNA was prepared by using LiCl precipitation (Sambrook et al, 2001) and poly(A+) RNA was extracted from 500 mg of total RNA using Oligotex columns (Qiagen, Hilden, Germany) according to the manufacturer's instructions. Starting from 1 mg of poly(A+) RNA, first-strand cDNA was synthesized by reverse transcription with a biotinylated oligo-dT25 primer (SEQ ID NO: 20) (Genset, Paris, France) and Superscript II (Life Technologies, Gaithersburg, MD). Second-strand synthesis was done by strand displacement with *Escherichia coli* ligase (Life Technologies), and DNA polymerase I (USB, Cleveland, Ohio) and RNAse-H (USB).
cDNA-AFLP Analysis.

Five hundred ng of double-stranded cDNA was used for AFLP analysis as described (Vos et al., Nucleic Acids Res. 23 (21) 4407-4414, 1995; Bachem et al., Plant J. 9 (5) 745-53, 1996). The restriction enzymes used were BstYI and MseI (Biolabs) and the digestion was done in two separate steps. After the first restriction digest with one of the enzymes, the 3' end fragments were collected on Dyna beads (Dynal, Oslo, Norway) by means of their biotinylated tail, while the other fragments were washed away. After digestion with the second enzyme, the released restriction fragments were collected and used as templates in the subsequent AFLP steps. For preamplifications, an MseI primer without selective nucleotides was combined with a BstYI primer containing either a T or a C as 3' most nucleotide. PCR conditions were as described (Vos et al., 1995). The obtained amplification mixtures were diluted 600-fold and 5 ml was used for selective amplifications using a P33-labeled BstYI primer and the Amplitaq-Gold polymerase (Roche Diagnostics, Brussels, Belgium). Amplification products were separated on 5% polyacrylamide gels using the Sequigel system (Biorad). Dried gels were exposed to Kodak Biomax films as well as scanned in a phosphoImager (Amersham Pharmacia Biotech, Little Chalfont, UK).
Characterization of AFLP Fragments.

Bands corresponding to differentially expressed transcripts, among which the (partial) transcript corresponding to CDS0689, were isolated from the gel and eluted DNA was reamplified under the same conditions as for selective amplification. Sequence information was obtained either by direct sequencing of the reamplified polymerase chain reaction product with the selective BstYI primer or after cloning the fragments in pGEM-T easy (Promega, Madison, Wis.) or sequencing of individual clones. The obtained sequences were compared against nucleotide and protein sequences present in the publicly available databases by BLAST sequence alignments (Altschul et al., Nucleic Acids Res. 25 (17) 3389-3402 1997). When available, tag sequences were replaced with longer EST or isolated cDNA sequences to increase the chance of finding significant homology. The physical cDNA done corresponding to CDS0689 was subsequently amplified from a commercial Tobacco cDNA library as follows.
Cloning of a Tobacco CDS0689 Seedy1 Gene (CDS0689)

A c-DNA library with average inserts of 1,400 by was made with poly(A+) isolated from actively dividing, non-synchronized BY2 tobacco cells. These library-inserts were cloned in the vector pCMVSPORT6.0, comprising an attB gateway cassette (Life Technologies). From this library 46,000 clones were selected, arrayed in 384-well microtiter plates, and subsequently spotted in duplicate on nylon filters. The arrayed clones were screened by using pools of several hundreds of radioactively labelled tags as probe (among which the BY2-tag corresponding to the sequence CDS0689). Positive clones were isolated (among which the done reacting with the BY2-tag corresponding to the sequence CDS0689), sequenced, and aligned with the tag sequence. Alternatively, when the hybridization with the tag would fail, the full-length cDNA corresponding to the tag was selected by PCR amplification as follows. Tag-specific primers was designed using primer3 program <genome.wi.mit.edu/genome_software/other/primer3.html>and used in combination with the common vector primer to amplify partial cDNA inserts. Pools of DNA from 50.000, 100.000, 150.000, and 300.000 cDNA clones were used as templates in the PCR amplifications. Amplification product were isolated from agarose gels, cloned, sequenced and aligned with tags. The vector comprising the sequence CDS0689 and obtained as described above, was referred to as entry clone.

Example 2

Vector Construction for Transformation with PRO0090-CDS0689 Cassette

The entry done was subsequently used in a Gateway™ LR reaction with p0830, a destination vector used for *Oryza sativa* transformation. This vector contains as functional elements within the T-DNA borders: a plant selectable marker; a plant screenable marker; and a Gateway cassette intended for LR in vivo recombination with the sequence of interest already cloned in the entry done. The rice prolamin RP6 promoter for endosperm-specific expression (PRO0090) is located upstream of this Gateway cassette.

Figure 2:
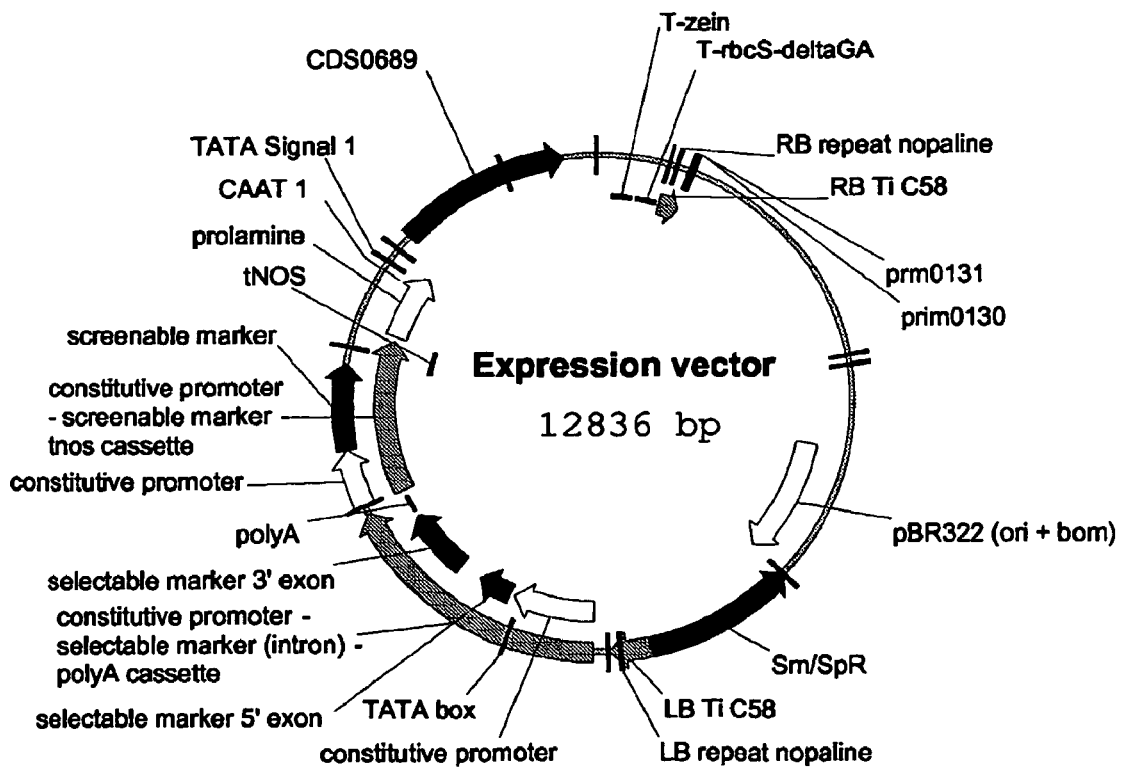
FIG. 2 is a map of the binary vector for the expression in *Oryza sativa* of the *Nicotiana tabacum* BY2 seedy1 gene (CDS0689) under the control of the rice prolamin RP6 promoter (PRO0090). This vector contains a T-DNA derived from the Ti Plasmid, limited by a left border (LB repeat, LB Ti C58) and a right border (RB repeat, RB Ti C58)). From the left border to the right border, this T-DNA contains: a selectable marker cassette for antibiotic selection of transformed plants; a screenable marker cassette for visual screening of transformed plants; the PRO0090-CDS0689-zein and rbcS-deltaGA double terminator cassette for expression of the *Nicotiana tabacum* BY2 seedy1 gene (CDS0689). This vector also contains an origin of replication from pBR322 for bacterial replication and a selectable marker (Spe/SmeR) for bacterial selection with spectinomycin and streptomycin.

After the LR recombination step, the resulting expression vector as shown in FIG. 2 was transformed into *Agrobacterium* and subsequently into *Oryza sativa* plants. Transformed rice plants were allowed to grow and then examined for various parameters as described in Example 3.

Example 3

Evaluation of Transgenic Rice Plants Transformed with Prolamin::Seedy1 (PRO0090-CDS0689) and Results Approximately 15 to 20 independent T0 rice transformants were generated. The primary transformants were transferred from tissue culture chambers to a greenhouse for growing and harvest of T1 seed. Four events of which the T1 progeny segregated 3:1 for presence/absence of the transgene were retained. For each of these events, approximately 10 T1 seedlings containing the transgene (hetero- and homo-zygotes), and approximately 10 T1 seedlings lacking the transgene (nullizygotes), were selected by monitoring screenable marker expression.

Two events (60 plants per event of which 30 positives for the transgene and 30 negative) having improved agronomical parameters in T1 were chosen for re-evaluation in T2. T1 and T2 plants were transferred to the greenhouse and evaluated for vegetative growth parameters and seed parameters, as described below.

Statistical Analysis: T-Test and F-Test

A two factor ANOVA (analysis of variants) was used as statistical model for the overall evaluation of plant phenotypic characteristics. An F-test was carried out on all the parameters measured, for all of the plants of all of the events transformed with the gene of interest. The F-test was carried out to check for an effect of the gene over all the transformation events and to determine the overall effect of the gene or "global gene effect". Significant data, as determined by the value of the F-test, indicates a "gene" effect, meaning that the phenotype observed is caused by more than the presence or position of the gene. In the case of the F-test, the threshold for significance for a global gene effect is set at a 5% probability level.

Vegetative Growth Measurements

The selected transgenic plants were grown in a greenhouse. Each plant received a unique barcode label to link unambiguously the phenotyping data to the corresponding plant. The selected transgenic plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity each plant was passed several times through a digital imaging cabinet and imaged. At each time point digital images (2048×1536 pixels, 16 million colours) were taken of each plant from at least 6 different angles. The parameters described below were derived in an automated way from all the digital images of all the plants, using image analysis software.

(a) Aboveground Plant Area

Plant aboveground area was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground.

b) Number of Primary Panicles

The tallest panicle and all the panicles that overlap with the tallest panicles when aligned vertically were counted manually, and considered as primary panicles.

Seed-Related Parameter Measurements

The mature primary panicles of T1 and T2 plants were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. This procedure resulted in the set of seed-related parameters described below.

(c) Number of Filled Seeds

The number of filled seeds was determined by counting the number of filled husks that remained after the separation step.

(d) Total Seed Yield Per Plant

The total seed yield was measured by weighing all filled husks harvested from a plant.

The results show % difference between positive plants and corresponding nullizygotes (negative) plants of a transgenic line. The values given in Tables 1 to 4 represent the average for two T1 lines and the same two T2 lines.

TABLE 1 overview of phenotypic data of seedy1 transgenic
T1 and T2 plants for above ground area

| | % difference between pos. and neg. plants for above ground area | |
|---|---|---|
| | T1 plants | T2 plants |
| 2 lines | +51% | |
| 2 lines | | +25.5% |

TABLE 2 overview of phenotypic data of seedy1 transgenic
T1 and T2 plants for number of first panicles

| | % difference between pos. and neg. plants for nr. of first panicles | |
|---|---|---|
| | T1 plants | T2 plants |
| 2 lines | +101% | |
| 2 lines | | +26.5% |

TABLE 3 overview of phenotypic data of seedy1 transgenic
T1 and T2 plants for number of filled seeds

| | % difference between pos. and neg. plants for nr. of filled seeds | |
|---|---|---|
| | T1 plants | T2 plants |
| 2 lines | +137% | |
| 2 lines | | +36.5% |

TABLE 4 overview of phenotypic data of seedy1 transgenic
T1 and T2 plants for total seed weight per plant

| | % difference between pos. and neg. plants for total seed weight per plant | |
|---|---|---|
| | T1 plants | T2 plants |
| 2 lines | +152% | |
| 2 lines | | +47% |

The invention claimed is:

1. A method for modifying the growth characteristics of a plant, comprising the steps of:
   (a) transforming plant cells from a plant with a genetic construct comprising a seedy1 nucleic acid sequence operably linked to a promoter, wherein the nucleic acid sequence encodes a seedy1 protein comprising the individual sequences in the following order from N-terminus to C-terminus: (i) the sequence according to SEQ ID NO 35; (ii) the sequence according to SEQ ID NO 16; (iii) the sequence according to SEQ ID NO 36 and (iv) the sequence according to SEQ ID NO 37, wherein the seedy1 nucleic acid consists essentially of a sequence having 90% sequence identity to SEQ ID NO:1;
   (b) expressing said seedy1 nucleic acid sequence in said transformed plant cells;
   (c) regenerating transgenic plants from said transformed plant cells; and
   (d) identifying a transgenic plant having a modified growth characteristic, wherein the growth characteristic is selected from the group consisting of: an increase in any or all of above-ground area, an increase in number of first panicles, an increase in total seed weight per plant and an increase in the number of filled seeds per plant compared to non-transformed plants.

2. The method according to claim 1, wherein said seedy1 nucleic acid sequence is of dicotyledonous plant origin from the family Solanaceae.

3. The method according to claim 2, wherein said promoter is a seed-preferred promoter.

4. The method according to claim 3, wherein said seed-preferred promoter is a prolamin promoter.

5. A plant or plant cell obtained by the method of claim 1.

6. A genetic construct comprising:(a) a seedy1 nucleic acid sequence encoding a seedy1 protein comprising the individual sequences in the following order from N-terminus to C-terminus: (i) the sequence according to SEQ ID NO 35; the sequence according to SEQ ID NO 16; (iii) the sequence according to SEQ ID NO 36 and (iv) the sequence according to SEQ ID NO 37, wherein the seedy1 nucleic acid consists essentially of a sequence having 90% sequence identity to SEQ ID NO:1; (ii) one or more tissue preferred control sequences capable of regulating expression of the nucleic acid sequence of (a); and optionally (c) a transcription termination sequence, wherein a plant transformed with said construct exhibits an increase in any or all of above-ground area, number of first panicles, number of filled seeds or an increase in total seed weight per plant compared to a non-transformed plant.

7. The construct according to claim 6, wherein said control sequence is a seed-specific promoter.

8. A plant or plant cell transformed with the construct according to claim 6.

9. The plant or plant cell according to claim 8, wherein said plant is a monocotyledonous plant such as sugar cane, or wherein the plant is a crop plant such as soybean, sunflower, canola, alfalfa, rapeseed, cotton, tomato, potato or tobacco, or wherein the plant is a cereal, such as rice, maize, wheat, barley, millet, rye, sorghum or oats.

10. Harvestable parts of a plant according to claim 8, wherein said harvestable parts are seeds and wherein the seeds comprise said genetic construct.

* * * * *

UNITED STATES PATENT AND TRADEMARK OFFICE
CERTIFICATE OF CORRECTION

PATENT NO.         : 7,932,432 B2                                Page 1 of 1
APPLICATION NO.    : 10/580085
DATED              : April 26, 2011
INVENTOR(S)        : Valerie Frankard et al.

It is certified that error appears in the above-identified patent and that said Letters Patent is hereby corrected as shown below:

In Claim 6, Column 72, line 19, after SEQ ID NO: 1; "(ii)" should read --(b)--.

Signed and Sealed this
Fourteenth Day of June, 2011

David J. Kappos
*Director of the United States Patent and Trademark Office*